US006517828B1

(12) United States Patent
Lin et al.

(10) Patent No.: US 6,517,828 B1
(45) Date of Patent: Feb. 11, 2003

(54) C-CAM AS AN ANGIOGENESIS INHIBITOR

(75) Inventors: Sue-Hwa Lin, Houston, TX (US); Weiping Luo, Pearland, TX (US); Christopher Logothetis, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/580,043

(22) Filed: May 26, 2000

Related U.S. Application Data

(60) Provisional application No. 60/136,563, filed on May 28, 1999.

(51) Int. Cl.$^7$ .......................... C12N 15/79; A61K 48/00
(52) U.S. Cl. ..................... 424/93.2; 536/23.5; 530/350; 435/320.1; 514/44
(58) Field of Search .......................... 536/23.5; 514/44; 435/320.1; 424/93.2; 530/350

(56) References Cited

FOREIGN PATENT DOCUMENTS

WO    WO 97/00954    1/1997

OTHER PUBLICATIONS

Kunath, T, et al, 1995, Inhibition of colonic tumor cell growth by biliary glycoprotein, Oncogene, vol. 11, No. 11, pp. 2375–2382.*
Lin, S–H, et al, Apr. 1999, Function and therapeutic implication of C–CAM cell–adhesion molecule in prostate cancer, Seminars in Oncology, vol. 26, No. 2, pp. 227–233.*
Chen, B, et al, 1997, The application of a novel tumor suppressor gene (C–CAM1) in human bladder cancer gene therapy (meeting abstract No. 1191), Journal of Urology, vol. 157, No. 4 (suppl.), p. 306.*
Kleinerman, DI, et al, 1996, Suppression of human bladder cancer growth by increased expression of C–CAM1 gene in an orthotopic model, Cancer Research, vol. 56, No. 15, pp. 3431–3435.*
Physicians' Desk Reference Electronic Library, Copyright ©2001 Medical Economics Company Inc., entry: TAXOL, pp. 1–43 (pages 1 and 2 only).*
Hsieh JT, et al, Prostate 1999 Sep. 15;41(1):31–8.*
Wang L, et al, Clinical Cancer Research 2000 Aug;6:2988–93.*
Estrera et al., "The cytoplasmic domain of C–Cam1 tumor suppressor is necessary and sufficient for suppressing the tumorigenicity of prostate cancer cells," Biochem. Biophys. Res. Comm., 263:797–803, 1999.
Huber et al., "The carboxyl–terminal region of biliary glycoprotein controls its tyrosine phosphorylation and association with protein–tyrosine phosphates SHP–1 and SHP–2 in Epithetal Cells," J. Bio. Chem., 274:335–344, 1999.

Aurivillius et al., "The cell adhesion molecule cell–CAM 105 is an ecto–ATPase and a member of the immunoglobulin superfamily," FEBS Lett., 264:267–269, 1990.
Cambier and Campbell, "Membrane immunoglobulin and its accomplices: new lessons from an old receptor," FASEB J., 6:3207–3217, 1992.
Cheung et al., "Structure and function of C–CAM1," J. Biol. Chem., 268:24303–24310, 1993.
Culic et al., "Molecular cloning and expression of a new rat liver cell–CAM 105 isoform," Biochem. J., 285:47–53, 1992.
Estrera et al., "The cytoplasmic domain of C–CAM1 tumor suppressor is necessary and sufficient for suppressing the tumorigenicity of prostate cancer cells," Biochem Biophys Res Commun, 263:797–803, 1999.
Fidler and Ellis, "Implications of angiogenesis for the biology and therapy of cancer metastasis," Cell, 79:185–188, 1994.
Fidler and Poste, "Cellular heterogeneity of malignant neoplasms: implications for adjuvant chemotherapy," Semin. Oncol. 12:207–221, 1985.
Fidler, "Modulation of the organ microenvironment for treatment of cancer metastasis," J. Natl. Cancer Inst., 87:1588–1592, 1995.
Folkman and Shing, "Angiogenesis," J. Biol. Chem., 267:10931–10934, 1992.
Folkman, "Angiogenesis in cancer, vascular, rheumatoid and other disease," Nature Medicine, 1:27–31, 1995.
Hanahan and Folkman, "Patterns and emerging mechanisms of the angiogenic swith during tumorigenesis," Cell., 86:353–64, 1996.
Hixson and McEntire, "Detection of an altered form of Cell–CAM105 on rat transplantable and primary hepatocellular carcinomas," Cancer Res., 49:6788–6794, 1989.
Hixson, et al., "Alterations in the expression of a hepatocyte cell adhesion molecule by transplantable rat hepatocellular carcinomas," Cancer Res., 45:3742–3749, 1985.
Hsieh et al., "Tumor suppressive role of an androgen–regulated epithelial cell adhesion molecule (C–CAM) in prostate carcinoma cell revealed by sense and antisense approaches," Cancer Res., 55:190–197, 1995.

(List continued on next page.)

Primary Examiner—Donna Wortman
Assistant Examiner—Stephen L. Rawlings
(74) Attorney, Agent, or Firm—Fulbright & Jaworski, L.L.P.

(57) ABSTRACT

The present invention relates generally to the fields hyperproliferative disease and angiogenesis. More particularly, the present invention demonstrates that a C-CAM1 cytoplasmic domain is necessary and sufficient for inhibiting angiogenesis. In particular embodiments, it relates to inhibiting hyperproliferative cell growth by administering to a cell a C-CAM1 cytoplasmic domain or an expression construct encoding a C-CAM1 cytoplasmic domain. In other embodiments, angiogenesis is inhibited by administering to a subject a C-CAM1 polypeptide or an expression construct encoding a C-CAM1 polypeptide.

9 Claims, 6 Drawing Sheets

OTHER PUBLICATIONS

Kleinerman et al., "Application of a tumor suppressor (C–CAM1)–expressing recombinant adenovirus in androgen–independent human prostate cancer therapy: A preclinical study," *Cancer Res.*, 55:2831–2836, 1995.

Lin and Guidotti, "Cloning and expression of a cDNA coding for a rat liver plasma membrane ecto–ATPase," *J. Biol. Chem.*, 264:14408–14414, 1989.

Lin et al., "Schedule–dependence of C–CAM1 adenovirus gene therapy in a prostate cancer model," *Anticancer Res*, 19:337–340, 1999.

Lin et al., "Immunochemical characterization of two isoforms of rat liver ecto–ATPase that show an immunological and structural identity with a glycoprotein cell–adhesion molecule with $M_r$ 105000," *Biochem. J.*, 278:155–161, 1991.

Luna and Hitt, "Cytoskeleton–plasma membrane interactions," *Science*, 258:955–964, 1992.

Luo et al., "Suppression of tumorigenicity of breast cancer cells by an epithelial cell adhesion molecule (C–CAM1): the adhesion and growth suppression are mediated by different domains," *Oncogene*, 1697–1704,. 1997.

Neumaier et al., "Biliary glycoprotein, a potential human cell adhesion molecule, is down–regulated in colorectal carcinomas," *Proc. Natl. Acad. Sci. USA*, 90:10744–10748, 1993.

Rak et al., "Consequences of angiogenesis for tumor progression, metastasis and cancer therapy," *Anticancer Drugs*, 6:3–18, 1995.

Rosenberg et al., "The expression of mouse biliary glycoprotein, a carcinoembryonic antigen–related gene, is down–regulated in malignant mouse tissues," *Cancer Res*, 53:4938–4945, 1993.

Rubinfeld et al., "Association of the APC gene product with β–Catenin," *Science*, 262:1731–1734, 1993.

Su et al., "Association of the APC tumor suppressor protein with catenins," *Science*, 262:1734–1737, 1993.

Takeichi, "Cadherin cell adhesion receptors as a morphogenetic regulator," *Science*, 251:1451–1455, 1991.

Trofatter et al., "A novel moesin–, ezrin–, radixin–like gene is a candidate for the neurofibromatosis 2 tumor suppressor," *Cell*, 72:791–800, 1993.

* cited by examiner

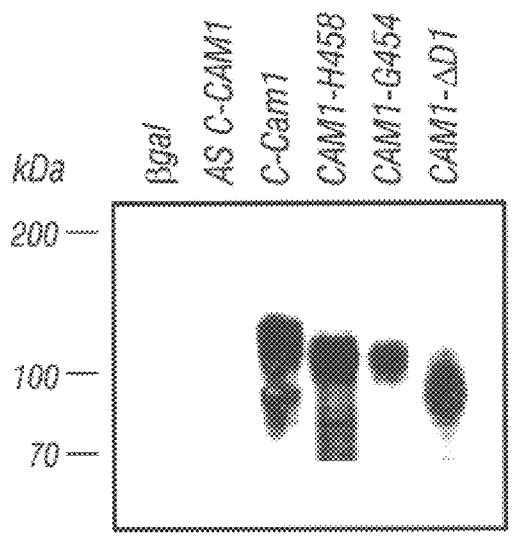 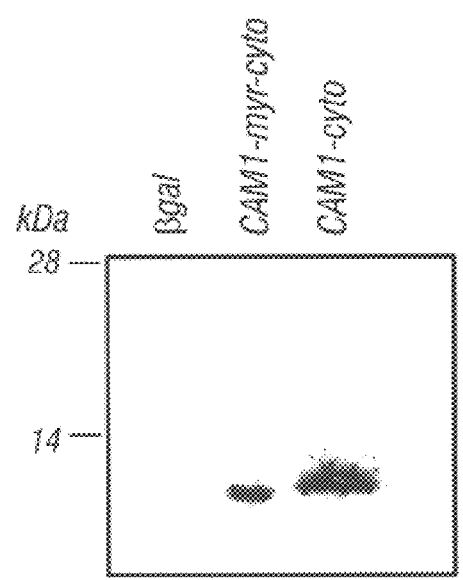
FIG. 4A
FIG. 4B

C-CAM AS AN ANGIOGENESIS INHIBITOR

The present application claims the benefit of U.S. Provisional Application Serial No. 60/136,563 filed on May 28, 1999. The entire text of the above-referenced disclosure is herein incorporated by reference. The U.S. government may own rights in this invention pursuant to grant number 5RO1 CA64856 from the National Cancer Institute.

BACKGROUND OF THE INVENTION

1. Field of the Invention

The present invention relates generally to the fields of cancer biology and molecular biology. More particularly, it relates to methods for inhibiting hyperproliferative cell growth and anti-angiogenic effects of C-CAM1.

2. Description of Related Art

Normal tissue homeostasis is achieved by an intricate balance between the rate of cell proliferation and cell death. Disruption of this balance, either by increasing the rate of cell proliferation or decreasing the rate of cell death, can result in the abnormal growth of cells and is thought to be a major event in the development of cancer. The effects of cancer are catastrophic, causing over half a million deaths per year in the United States alone. Conventional strategies for the treatment of cancer, chemotherapy, radiotherapy, surgery, biological therapy or combinations thereof are often ineffective.

In nearly 50% of patients, surgical excision of primary neoplasms is ineffective because metastasis has occurred by the time the tumor is large enough for resection (Sugarbaker, 1977; Fidler and Balch, 1987). Metastases can be located in different organs as well as different regions of the same organ, making complete eradication by surgery, radiation, drugs, or biotherapy difficult. Furthermore, the organ microenvironment significantly influences the response of tumor cells to therapy (Fidler, 1995), as well as the efficiency of anticancer drugs, which must be delivered to tumor foci in amounts sufficient to destroy cells without leading to undesirable side effects (Fidler and Poste, 1985). In addition, the treatment of metastatic cancer is greatly hindered due to the biological heterogeneity of cancer cells, and the rapid emergence of tumor cells that become resistant to most conventional anticancer agents (Fidler and Poste, 1985).

Conventional therapy for malignancy, such as chemotherapy and radiation, has focused on mass cell killing without specific targeting, often resulting in damaging side effects. With advances in molecular genetics and biology, it has become evident that altered expression of normal genes leads to initiation of cancer cells. Cells can be regulated in a positive (stimulatory) or negative (suppressive) manner. Loss of negative regulation of cell growth is often found in malignant cells which exhibit loss of cell proliferation control. Most negative regulators (Marx, 1993; Grunicke and Maly, 1993), referred to as tumor suppressors, have been found to be involved either in direct control of the cell cycle (e.g., Rb, p53, WT-1) or in the signaling pathway leading to cell growth and differentiation (e.g., NF-1).

Thus, the new direction in cancer therapy is to deliver a normal gene to replace or correct the mutated gene, thereby altering the malignant phenotype of transformed cells. However, the transfer of genetic material into cells has limitations. As such, there clearly remains a need for improved methods of anti-hyperproliferative cell therapy.

SUMMARY OF THE INVENTION

The present invention addresses the need for improved compositions and methods for anti-hyperproliferative and anti-angiogenic cell therapies. In one embodiment, an objective of the present invention is to provide a composition comprising a cytoplasmic domain of C-CAM1, free from other C-CAM1 domains. In particular embodiments, a composition comprising a cytoplasmic domain of C-CAM1, is provided, wherein the cytoplasmic domain has or comprises the sequence of SEQ ID NO:1. In addition to providing C-CAM1 to a cell or subject, the methods of the invention may further include one or more additional antihyperproliferative or anti-angiogenic therapies, such as surgery, chemotherapy, radiotherapy, hormone therapy, immunotherapy, or gene therapy with other therapeutic genes.

In certain embodiments, a cytoplasmic domain of C-CAM1 further comprises a non-C-CAM1 molecule. In other embodiments, a cytoplasmic domain of C-CAM1 comprises a non-C-CAM1 molecule, wherein the non-C-CAM1 molecule is linked to the C-CAM1 cytoplasmic domain. In additional embodiments, the non-C-CAM1 molecule is selected from the group consisting of a tumor suppressor, an inducer of apoptosis, a cytokine, a targeting sequence, a single chain antibody, an antisense construct, a ribozyme and a chemotherapeutic agent. In one embodiment, the non-C-CAM1 molecule is a tumor suppressor selected from the group consisting of p53, p16, p21, MMAC1, p73, zac1, BRCAI, and Rb. In another embodiment, the non-C-CAM1 molecule is an the inducer of apoptosis selected from the group consisting of Bax, Bak, Bim, Bik, Bid, Bad, Harakiri, Ad E1B, and an ICE-CED3 protease. In yet other embodiments, the non-C-CAM1 molecule is a cytokine selected from the group consisting of IL-2, IL-2, IL-3, IL-4, IL-5, IL-6, IL-7, IL-8, IL-9, IL-10, IL-11, IL-12, IL-13, IL-14, IL-15, TNF, GMCSF β-interferon, and γ-interferon. In still further embodiments, the non-C-CAM1 molecule is a target sequence, wherein the target sequence is a substrate for integrins, proteoglycans, glycoproteins, cell surface receptors, nuclear receptors, or transporters. In a particular embodiment, the non-C-CAM1 molecule is a chemotherapeutic agent, wherein the chemotherapeutic agent is selected from the group consisting of verapamil, podophyllotoxin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, TAXOL (paclitaxel), transplatinum, 5-fluorouracil, vincristine, vinblastine, and methotrexate.

In certain embodiments, the invention involves methods of inhibiting a hyperproliferative cell by administering a C-CAM1 cytoplasmic domain, free from other C-CAM1 domains, to the cell such that the domain inhibits hyperproliferative cell growth. In particular embodiments, the hyperproliferative cell may be a cancer cell, wherein the cancer is selected from the group consisting of lung, breast, melanoma, colon, renal, testicular, ovarian, lung, prostate, hepatic, germ cancer, epithelial, prostate, head and neck, pancreatic cancer, glioblastoma, astrocytoma, oligodendroglioma, ependymomas, neurofibrosarcoma, meningia, liver, spleen, lymph node, small intestine, blood cells, colon, stomach, thyroid, endometrium, prostate, skin, esophagus, bone marrow, and blood. It is contemplated that any of the compounds of the invention may be administered as a pharmaceutical composition to a cell or subject. Components of the composition are pharmaceutically acceptable and are described elsewhere in this disclosure.

In further embodiments, the invention concerns methods of inhibiting a hyperproliferative cell by administering a C-CAM1 cytoplasmic domain, free from other C-CAM1 domains, to the cell, and by also administering a second anti-hyperproliferative agent. The second anti-hyperproliferative agent may be selected from the group consisting of tumor irradiation, chemotherapeutic agent, and a nucleic acid encoding an anti-hyperproliferative polypeptide. In one embodiment, the second anti-hyperproliferative agent is a chemotherapeutic agent selected from the group consisting of verapamil, podophyllotoxin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, TAXOL (paclitaxel), transplatinum, 5-fluorouracil, vincristine, vinblastine, and methotrexate. In another embodiment, the second anti-hyperproliferative agent is radiation, selected from the group consisting of X-ray radiation, UV-radiation, γ-radiation, or microwave radiation In a further embodiment, the second anti-hyperproliferative agent is a polypeptide selected from the group consisting of p53, p16, p21, MMAC1, p73, zac1, BRCAI, Rb, Bax, Bak, Bim, Bik, Bid, Bad, Harakiri, Ad E1B, and an ICE-CED3 protease.

In other embodiments of the invention, methods involve a polypeptide that comprises a C-CAM1 cytoplasmic domain, which may be delivered endoscopically, intratracheally, intralesionally, percutaneously, intravenously, aerosolized, intradermally, subcutaneously, intraendothelially, intratumorally, intraperitoneally, intramuscularly, intraendothelially, regionally, locally, or topically.

In another embodiment of the present invention, methods of inhibiting a hyperproliferative cell involve administering an expression construct containing a first C-CAM1 polynucleotide encoding a C-CAM1 cytoplasmic domain, but no other C-CAM1 domains, in an amount effective to inhibit a hyperproliferative cell. The polynucleotide may be linked to a promoter that is operable in eukaryotic cells, which allows the promoter to direct the expression of the C-CAM1 cytoplasmic domain. In particular embodiments, the hyperproliferative cell may be a cancer cell, wherein the cancer is selected from the group consisting of lung, breast, melanoma, colon, renal, testicular, ovarian, lung, prostate, hepatic, germ cancer, epithelial, prostate, head and neck, pancreatic cancer, glioblastoma, astrocytoma, oligodendroglioma, ependymomas, neurofibrosarcoma, meningia, liver, spleen, lymph node, small intestine, blood cells, colon, stomach, thyroid, endometrium, prostate, skin, esophagus, bone marrow, and blood. In other embodiments, inhibiting a hyperproliferative cell by administering an expression construct comprising a first C-CAM1 polynucleotide encoding a C-CAM1 cytoplasmic domain, linked to a promoter operable in eukaryotic cells, further comprises administering a second anti-hyperproliferative agent. In particular embodiments, the anti-hyperproliferative agent is chemotherapeutic DNA damaging agent selected from the group consisting of verapamil, podophyllotoxin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, TAXOL (paclitaxel), transplatinum, 5-fluorouracil, vincristine, vinblastine, and methotrexate. In yet other embodiments, the anti-hyperproliferative agent is tumor irradiation, wherein the radiation is selected from the group consisting of X-ray radiation, UV-radiation, γ-radiation, and microwave radiation. In further embodiments, the second polynucleotide encoding a anti-hyperproliferative gene is selected from the group consisting of p53, p16, p21, MMAC1, p73, zac1, BRCAI, Rb, Bax, Bak, Bim, Bik, Bid, Bad, Harakiri, Ad E1B, and an ICE-CED3 protease.

In particular embodiments, the second polynucleotide is operatively linked to a promoter in the first expression construct, wherein the promoter is selected from the group consisting of CMV IE, human or murine MHC class II, SV40, RSV LTR, HIV-1 and HIV-2 LTR. Alternatively, the polynucleotide is operatively linked to a promoter in a second expression construct.

In certain embodiments, the first expression construct is selected from the group consisting of an adenovirus, an adeno-associated virus, a vaccinia virus, and a herpes virus. In yet other embodiments, the first expression construct is non-viral. In other embodiments, the second expression construct is selected from the group consisting of an adenovirus, an adeno-associated virus, a vaccinia virus and a herpes virus, wherein the promoter is selected from the group consisting of CMV IE, human or murine MHC class II, SV40, RSV LTR, HIV-1 and HIV-2 LTR. In yet other embodiments the second expression construct is non-viral. In another embodiment, the administering comprises delivering the expression construct endoscopically, intratracheally, intralesionally, percutaneously, intravenously, aerosolized, intradermally, subcutaneously, intraendothelially, or intratumorally.

In another embodiment of the present invention, methods of inhibiting angiogenesis in a subject involve administering an isolated C-CAM1 polypeptide to a subject in an amount effective to inhibit angiogenesis. It is contemplated that the subject may be a mammal, such as a human. In one embodiment, the C-CAM1 polypeptide is a C-CAM1 cytoplasmic domain free from other C-CAM1 domains. In another embodiment, the C-CAM1 polypeptide is a C-CAM1 cytoplasmic domain free from other C-CAM1 domains wherein the C-CAM1 polypeptide has the sequence of SEQ ID NO:1. In yet another embodiment, administration of a C-CAM1 cytoplasmic domain comprises delivering the polypeptide endoscopically, intratracheally, percutaneously, intravenously, aerosolized, intradermally, subcutaneously, or intraendothelially.

In another embodiment of the invention, a method for inhibiting angiogenesis in a subject comprising the step of administering an expression construct comprising a C-CAM1 polynucleotide encoding a C-CAM1, linked to a promoter operable in eukaryotic cells, wherein the promoter directs the expression of the C-CAM1, which inhibits angiogenesis. In certain embodiments, a C-CAM1 polynucleotide encoding a C-CAM1 encodes a C-CAM1 cytoplasmic domain free from other C-CAM1 domains. In still other embodiments, a C-CAM1 polynucleotide encoding a C-CAM1 encodes a C-CAM1 cytoplasmic domain free from other C-CAM1 domains encodes a C-CAM1 cytoplasmic domain having the sequence of SEQ ID NO:1. In certain embodiments, the expression construct is selected from the group consisting of an adenovirus, an adeno-associated virus, a vaccinia virus and a herpes virus. In other embodiments, the expression construct is non-viral. In yet other embodiments the promoter is selected from the group consisting of CMV IE, human or murine MHC class II, SV40, RSV LTR, HIV-1, and HIV-2 LTR. In another embodiment, administering comprises delivering the expression construct endoscopically, intratracheally, percutaneously, intravenously, aerosolized, intradermally, subcutaneously, intraperitoneally, intramuscularly, intraendothelially, regionally, locally, or topically.

The compositions involved in the methods of the invention may be administered to a cell or subject in an amount effective to render treatment to the cell or subject. In the context of the invention, it is contemplated that the following constitute treatment, though the invention is not limited to these examples: inhibition of angiogenesis, inhibition or suppression of a hyperproliferative cell, which includes inhibiting its growth and or tumorigenicity, as well as inhibition of tumor progression or cancer.

Other methods of the invention include methods of treating a subject with a tumor by giving the patient a composition that contains either (1) an isolated C-CAM1 polypeptide or (2) an expression construct comprising a nucleic acid sequence encoding a C-CAM1 polypeptide under the control of a promoter operable in a eukaryotic cell, in an amount effective to inhibit angiogenesis around the tumor. This may be done in conjunction with tumor resection, which may be performed after or during the treatment with C-CAM-1; alternatively, treatment with C-CAM1 may occur after of all or part of a tumor has been resected, in which case the C-CAM1 is administered to the remaining tumor or tumor bed. Other anti-proliferative treatment may be employed in conjunction with any of the C-CAM1 methods described herein.

Also included are methods that take advantage of any bystander effect of C-CAM1. Therefore, methods for treating a patient with cancer may involve administering to a noncancerous or nonhyperproliferative cell in the patient an effective amount of a composition to confer a therapeutic benefit on the patient. The composition would contain a nucleic acid sequence encoding a C-CAM1 polypeptide under the control of a promoter operable in a eukaryotic cell or a C-CAM1 polypeptide that included the cytoplasmic domain, with or without other C-CAM1 domains. The term "therapeutic benefit" used throughout this application refers to anything that promotes or enhances the well-being of the patient with respect to the medical treatment of his hyperproliferative disease. A list of nonexhaustive examples of this includes extension of the patient's life by any period of time; decrease or delay in the neoplastic development of the disease; decrease in hyperproliferation; reduction in tumor growth; delay of metastases; reduction in the proliferation rate of a cancer cell, tumor cell, or any other hyperproliferative cell; induction of apoptosis in any treated cell or in any cell affected by a treated cell; and a decrease in pain to the patient that can be attributed to the patient's condition.

As used in the specification, "a" or "an" may mean one or more. As used in the claim(s), the words "a" or "an" may mean one or more than one when used in conjunction with the word "comprising." As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 3A) Adenovirus genome structure. The adenovirus 5 genome is about 36 kb and is divided into 100 mu (1 mu=0.36 kb) (Graham and Prevec, 1991). The C-CAM genes were expressed from the human cytomegalovirus promoter. The entire expression cassette, including the cytomegalovirus promoter, C-CAM cDNAs, and simian virus 40 early polyadenylation signal, was used to replace the E1 region (1.3–9.2 mu). The relative locations of the PCR primers are shown. (FIG. 3B) Gel analysis of PCR products. The viral DNA was extracted and prepared according to procedures described by Zhang et al. (1993). Primers XCMV1 and XCMV2, which flank the recombinant cDNA sequence, were used to detect the cDNA insert. The expected sizes of the PCR products are indicated.

FIG. 4A and FIG. 4B. Immunoblot analysis of C-CAM1 mutant proteins expressed in DU145 cells. DU145 cells were infected with recombinant adenovirus at an MOI of 10 for 48 h. The cell lysates were prepared and analyzed on a 10% (FIG. 4A) or 15% SDS-polyacrylamide gel (FIG. 4B). Cell lysates from Ad β-gal infected cells was used as control. The recombinant viruses used are indicated at the top of each lane. (FIG. 4A) Immunoblot with antibody Ab669 (Lin et al., 1991) diluted 1:1000. (FIG. 4B) Immunoblot with anti-peptide antibody anti-C3 (Lin et al., 1991) diluted 1:500.

DESCRIPTION OF ILLUSTRATIVE EMBODIMENTS

Figure 1A:
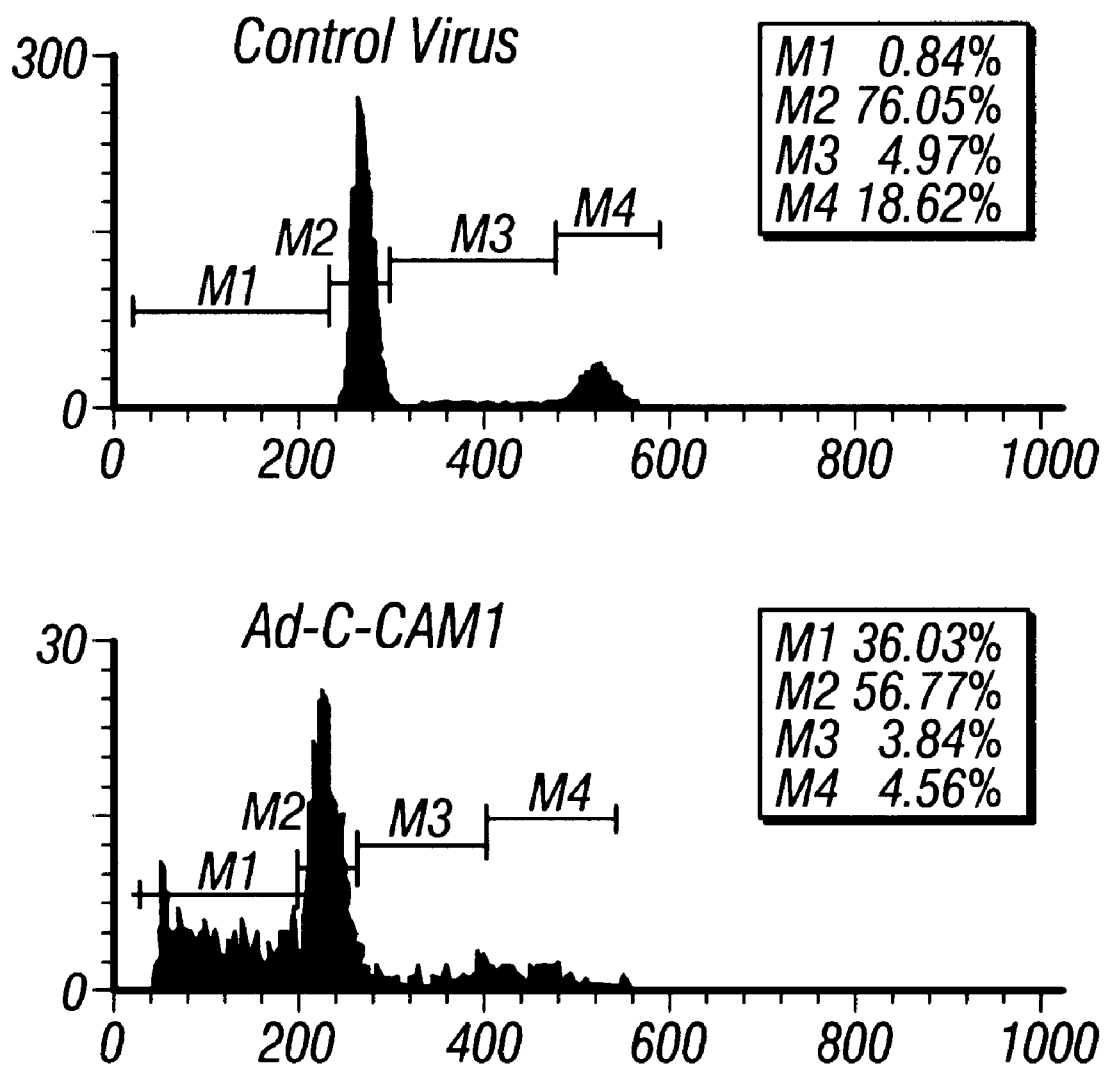
FIG. 1A. Effect of the conditioned media derived from the Ad-C-CAM1 or control virus-infected cells on apoptosis of human pulmonary artery endothelial cells. DNA content frequency distribution histograms representing apoptotic cells.

Disruption in the balance of normal tissue homeostasis, either by increasing the rate of cell proliferation or decreasing the rate of cell death, can result in the abnormal growth of cells and is thought to be a major event in the development of cancer. The effects of cancer are catastrophic, causing over half a million deaths per year in the United States alone. Conventional strategies for the treatment of cancer, chemotherapy, radiotherapy, surgery, biological therapy or combinations thereof are often ineffective.

Cells can be regulated in a positive (stimulatory) or negative (suppressive) manner. Loss of negative regulation of cell growth is often found in malignant cells which exhibit loss of cell proliferation control. Most negative regulators (Marx, 1993; Grunicke and Maly, 1993), referred to as tumor suppressors, have been found to be involved either in direct control of the cell cycle (e.g., Rb, p53, WT-1) or in the signaling pathway leading to cell growth and differentiation (e.g., NF-1).

C-CAMs are glycoproteins of the immunoglobulin (Ig) gene family (Lin et al, 1991) that recently have been characterized as tumor suppressors (Luo et al., 1997). They were originally identified by their ability to mediate hepatocyte aggregation or adhesion (Ocklind and Obrink, 1982). In addition to cell-adhesion activity, several other lines of evidence also implicate C-CAMs in growth suppression of tumors of epithelial origin and might be essential for maintaining normal cell growth and differentiation (Hixson & McEntire, 1989; Hixson et al., 1985; Luo et al., 1997).

The present invention demonstrates that, in addition to C-CAM's cell-adhesion activity and tumor suppressive properties, the polypeptide plays a role in inhibiting angiogenesis. It is further demonstrated by the inventors that a cytoplasmic domain of C-CAM1 is necessary and sufficient to inhibit angiogenesis.

Angiogenesis, the formation of new capillaries from pre-existing vessels, is essential for tumor progression (Folkman and Shing, 1992; Fidler and Ellis, 1994; Folkman, 1995; Hanahan and Folkman, 1996; Rak et al., 1995). al., 1998). Although tumors of 1–2 mm in diameter can receive all nutrients by diffusion, further growth depends on the development of an adequate blood supply through angiogenesis.

The present invention contemplates, in one embodiment, inhibiting hyperproliferative cell growth by administering to the cell a C-CAM1 cytoplasmic domain or an expression construct encoding a C-CAM1 cytoplasmic domain. In other embodiments, the inhibition of angiogenesis is contemplated. In these embodiments, a subject is administered a C-CAM1 polypeptide or an expression construct encoding a C-CAM1 polypeptide to inhibit angiogenesis.

A. C-CAM

C-CAMs are glycoproteins of the immunoglobulin (Ig) gene family (Lin et al., 1991). They were originally identified by their ability to mediate hepatocyte aggregation (Ocklind and Obrink, 1982). Molecular cloning of C-CAM1, one of the isoforms, revealed that C-CAM1 has four Ig-like extracellular domains, a transmembrane domain, and a cytoplasmic domain of 71 amino acids. Structure and function analysis of C-CAM1 revealed that only the first extracellular Ig domain is important for its adhesion function (Cheung et al., 1993a).

Throughout the application, the term C-CAM is intended to refer to the rat C-CAM or cell-CAM 105, the human C-CAM homologue (biliary glycoprotein 1 (BGP1)), and all C-CAM homologues from other species. Similarly, throughout the application, the term C-CAM is intended to refer to polypeptide sequences from human (SEQ ID NO:1), mouse (SEQ ID NO:2), rat (SEQ ID NO:3) and all C-CAM cytoplasmic domain homologues from other species.

1. C-CAM Protein Structure

C-CAM, like all other known cell adhesion molecules (CAMs), are large intrinsic cell-surface glycoproteins that are mobile in the plane of the membrane (Gall and Edelman 1981; Pollerberg et al., 1986). CAMs mediate cell recognition and adhesion and are of prime importance for the formation and integrity of tissues. The majority of the known CAMs belong to one of the following families: the immunoglobulin (Ig) superfamily (Williams et al., 1988), the cadherin family (Takeichi, 1988), the integrin superfamily (Hynes, 1987), the LEC-CAM family (Stoolman, 1989) and the H-CAM family (Stoolman, 1989). The cell adhesion molecule C-CAM belongs to the immunoglobulin superfamily, and more specifically is a member of the carcinoembryonic antigen (CEA) gene family.

The Ig-superfamily is a large family that, in addition to the immunoglobulins, contains many other proteins, the majority being involved in cellular recognition phenomena (Williams et al., 1988). The common building block is the immunoglobulin domain of about 100 amino acid residues that is arranged as a sandwich of two sheets of anti-parallel β-strands. Different members of the superfamily have varying numbers of Ig-like domains. A list of putative CAMs presently known, which belong to the Ig-superfamily, is given in Table 1. One characteristic feature of CAMs in the Ig-superfamily is that they are calcium-independent, that is, they do not need calcium ions for their binding activity. Both homophilic and heterophilic binding occur among the members of this family.

There seem to be several subfamilies of CAMs in the Ig-superfamily. One of these is the carcinoembryonic antigen (CEA) family (Benchimol et al., 1989), which contains a large number of different proteins that can be either transmembrane, GPI-linked, or secreted (Khan et al., 1989). Several of the members of the CEA family cross-react immunologically. It has been reported that both CEA itself, which has seven Ig-domains, and NCA (nonspecific cross-reactive antigen), which has three Ig-domains, can function both as homophilic and heterophilic, calcium-independent cell adhesion molecules (Benchimol et al., 1989; Oikawa et al., 1989).

A close examination of the amino acid sequence of rat C-CAM reveals that it is a member of the immunoglobulin superfamily (Aurivillius et al., 1990). Lin and Guidotti noted that the ecto-ATPase/C-CAM is highly homologous to human biliary glycoprotein 1 (BGP1), with 65% of the amino acids being identical (Lin et al., 1989). BGP1 is a member of the CEA-family (Aurivillius et al., 1990; Lin et al., 1989). Thus, it has been concluded that C-CAM belongs to the CEA-subfamily of the immunoglobulin superfamily.

So far, two C-CAM isoforms, C-CAM1 and C-CAM2, have been identified. Both isoforms are composed of a cytoplasmic domain, a 25 amino acid long transmembrane domain, and an extracellular domain with four Ig-like domains. Sixteen potential sites for N-glycosylation are found in the extracellular domain, a finding that agrees well with the chemical determination of the carbohydrate content in the mature protein (Obrink 1991). C-CAM1 and C-CAM2 differ in their first Ig domains by 16 amino acids and in the length of their cytoplasmic domains (Culic et al., 1992). C-CAM1, but not C-CAM2, shows adhesion activity when expressed in a baculoviral vector in insect cells (Cheung et al., 1993a). C-CAM binds to itself in a homophilic manner. Further structural and functional analyses of C-CAM1 by Cheung et al. (1993a) indicated that the presence of the first Ig domain is essential for adhesion.

TABLE 1

CAMs in the Ig-superfamily

| CAM | Cell Type | Species | References |
| --- | --- | --- | --- |
| N-CAM | Neuron, glia muscle | Mammals, birds, amphibians | Williams et al, 1988 Hansson et al., 1990 |
| L-1 Ng-CAM NILE G4 MAG | Neuron Ep Gila | Mouse, rat, chicken Man, mouse, rat, chicken, cow | Moos et al., 1988 Salzer et al., 1987 |
| Po | Schwann | Rat | Lemke et al., 1988 |
| Contactin | Neuron | Chicken | Ranscht, 1988 |
| F11 | Neuron | Chicken | Brümmendorf et al., 1989 |
| F3 | Neuron | Mouse | Gennarini et al., 1989 |

TABLE 1-continued

CAMs in the Ig-superfamily

| CAM | Cell Type | Species | References |
|---|---|---|---|
| Fasciclin II | Neuron | Grasshopper | Harrelson et al, 1988 |
| Neuroglian | Neuron, glia, many other cell types | Drosophila | Bieber et al., 1989 |
| Amalgam | Neuron | Drosophila | Seeger et al., 1988 |
| TAG-1 | Neuron | Rat | Furley et al., 1990 |
| C-CAM | Ep. En. Lc. | Rat, man | Odin et al., 1988; Tingstrom et al., 1990; Aurivillius et al., 1990 |
| CEA | Ep. | Man | Benchimol et al., 1989 |
| NCA | Ep. Lc. | Man | Oikawa et al., 1989 |
| DCC | Ep. | Man | Fearoz et al., 1990 |
| GP42 | Fibroblast | Mouse | Altruda et al., 1989 |
| MUC18 | Melanoma | Man | Lehmann et al., 1989 |
| PECAM1/End | Lc. En. 5M. Trc | Man, cow | Newman el al., 1990 |
| o-CAM/CD31 | En | Man | Elices et al., 1990 |
| VCAM1/ | Lc. many cell types | Man, mouse | Staunton et al., 1988 |
| INCAM-110 | | Man | Staunton et al., 1989 |
| ICAM1/CD54 | En | Man | Streuli et al., 1988 |
| ICAM-2 | Ly. kidney, prostate | | |
| LAR | | | |
| CD2 | Ly | Man | Williams and Barclay, 1988 |
| LFA-3/CD58 | Many cell types | Man | Williams and Barclay, 1988 |
| CD4 | Ly | Man, mouse | Williams and Barclay, 1988 |
| CD8 | Ly | Man, mouse | Williams and Barclay, 1988 |
| MHC I | All kinds | Man, mouse, etc. | Williams and Barclay, 1988 |
| MHC II | Mo. dendritic | Man, mouse, etc. | Williams and Barclay, 1988 |
| TCR | T-cells | Man, mouse, etc. | Williams and Barclay, 1988 |
| CD28 | T-cells | Man | Linsley et al., 1990 |
| B7/BB-1 | B-cells | Man, mouse | Linsley el al., 1990 |
| B29 | B-cells | Mouse | Hermanson et al., 1988 |

2. C-CAM Location and Function

C-CAM antigens are expressed in a number of organs of mature rats (Odin et al., 1988). The tissue distribution within these organs is, however, limited. Thus, C-CAM is primarily expressed in various epithelia (including hepatocytes of the liver), endothelia of capillaries, small arteries and veins, and in megakaryocytes, platelets, polymorphonuclear leukocytes and a subset of mononuclear leukocytes (Odin et al., 1988). It has not been found in nervous tissues, muscle tissues or connective tissues.

C-CAM appears rather late in the fetal development of the liver and goes through transient down-regulation during regeneration after partial hepatectomy (Odin et al., 1986). In this context, it is also interesting to note that the expression of C-CAM is significantly altered in hepatocellular carcinomas, so that it is either missing or chemically modified (Hinson et al., 1985; Hinson et al., 1989). In addition, Rosenberg et al. (1993) and Neumaier et al. (1993) demonstrated that mouse and human biliary glycoprotein, a C-CAM homologue, is down-regulated in colon tumors. It is demonstrated in Example 7 in the present invention that not only does C-CAM1 suppress tumorigenicity of prostate cancer cells, but also that the cytoplasmic domain of C-CAM1 is necessary and sufficient for suppressing the tumorigenicity.

3. C-CAM Mechanism of Action

Although the mechanisms by which C-CAM affects these processes are not clear, these cell-surface adhesion molecules most likely exert their biological effects through interactions with other cellular molecules, that transduce outside signals into the cells. For example, the integrins, which are $Ca^{2+}$-dependent CAMs known to interact with a variety of extracellular matrices, have been shown to associate with several intracellular tyrosine kinases (Luna and Hitt, 1992). On the other hand, CAMs have also been shown to participate in the organization of cell architecture by connecting cytoskeleton molecules through an adherens-junction protein complex. Recent molecular genetic analyses (Trofatter et al., 1993) suggest that a potential tumor suppressor gene (NF-2) involved in neurofibromatosis belongs to the family of adherens junction molecules. Also, in the case of E-cadherin, at least three cytoplasmic proteins, $\alpha$-, $\beta$-, and $\gamma$-catenin, are associated with the cytoplasmic domain of cadherin (Takeichi, 1991). These associated proteins, which are part of the adherens junction proteins, play important roles in maintaining cellular architecture (Geiger, 1983). Consistent with this observation, recently it was found that $\alpha$- and $\beta$-catenin were also associated with the product of a potential tumor suppressor gene involved in colon carcinogenesis, APC (Rubinfeld et al., 1993; Su et al., 1993). These observations suggest that a cell-adhesion molecule can regulate cell growth through indirect interactions with a tumor suppressor.

C-CAMs suppression of tumorigenicity and adhesive properties are mediated by different domains (Luo et al., 1997). The cytoplasmic domain of C-CAM1 contains several potential phosphorylation sites, including one for cAMP-dependent kinase and one for tyrosine kinase. The putative tyrosine phosphorylation sequence is also within the consensus sequence for the antigen-receptor homology domain (Cambier and Campbell, 1992) that is postulated to be important for signal transduction from membrane-bound IgM molecules in B cells. These structural features suggest that the cytoplasmic domain of C-CAM1 may be critical for signal transduction and that C-CAM1 may interact with other kinases to elicit a negative signal for cell growth. C-CAM1 has been observed to function as a growth suppressor in prostate cancer cells (Hsieh et al., 1995; Kleinerman et al., 1995), and more recently, the cytoplasmic domain of C-CAM1 has been identified as critical for growth suppression of breast cancer cells in vivo (Luo et al., 1997). Examples 2–7, disclosed herein, demonstrate that the cytoplasmic domain of C-CAM1 is necessary and sufficient for suppressing cancer cell proliferation and inhibiting angiogenesis.

B. Engineering Expression Constructs

In particular embodiments, it may be necessary to make recombinant C-CAM1 or C-CAM1 cytoplasmic domain, alternatively, the C-CAM1 or C-CAM1 cytoplasmic domain used for therapeutic applications may be presented as C-CAM1 or C-CAM1 cytoplasmic domain gene in an expression construct for C-CAM1 or C-CAM1 cytoplasmic domain based gene therapy. These embodiments involve the manipulation of genetic material to produce expression constructs that encode C-CAM1 or C-CAM1 cytoplasmic domain. Such methods involve the generation of expression constructs containing, for example, a heterologous DNA encoding a gene and a means for its expression, replicating the vector in an appropriate helper cell, obtaining viral particles produced therefrom, and infecting cells with the recombinant virus particles. The following discussion is directed toward engineering expression constructs for recombinant protein production and/or gene therapy.

The gene will be a therapeutic gene that encodes a C-CAM1 or C-CAM1 cytoplasmic domain protein, or the gene may be a second therapeutic gene or nucleic acid useful in the treatment of, for example, cancer cells. In the context of gene therapy, the gene will be a heterologous DNA, meant to include DNA derived from a source other than the viral genome which provides the backbone of the vector. Finally, the virus may act as a live viral vaccine and express an antigen of interest for the production of antibodies thereagainst. The gene may be derived from a prokaryotic or eukaryotic source such as a bacterium, a virus, a yeast, a parasite, a plant, or even an animal. The heterologous DNA also may be derived from more than one source, i.e., a multigene construct or a fusion protein. The heterologous DNA also may include a regulatory sequence which may be derived from one source and the gene from a different source.

1. Control Regions a. Promoters

Throughout this application, the term "expression construct" is meant to include any type of genetic construct containing a nucleic acid coding for gene products in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding genes of interest.

The nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of Drosophila, and when ecdysone or an analog such as muristerone A binds to the receptor, the receptor activates a promoter to turn on expression of the downstream transgene high levels of mRNA transcripts are attained. In this system, both monomers of the heterodimeric receptor are constituitively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (CLONTECH, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of *E. coli*. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constituitively on. In the Tet-On™ system, the tetracycline repressor is not wild type and in the presence of doxycycline activates transcription. For gene therapy vector production, the Tet-Off™ system would be preferable so that the producer cells could be grown in the presence of tetracycline or doxycycline and prevent expression of a potentially toxic transgene, but when the vector is introduced to the patient, the gene expression would be constituitively on.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly, tissue-specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, the following promoters may be used to target gene expression in other tissues (Table 2).

TABLE 2

Tissue-specific promoters

| Tissue | Promoter |
| --- | --- |
| Pancreas | insulin |
|  | elastin |
|  | amylase |
|  | pdr-1 pdx-1 |
|  | glucokinase |
| Liver | albumin PEPCK |
|  | HBV enhancer |
|  | alpha fetoprotein |
|  | apolipoprotein C |
|  | alpha-1 antitrypsin |
|  | vitellogenin, NF-AB |
|  | Transthyretin |
| Skeletal muscle | myosin H chain |
|  | muscle creatine kinase |
|  | dystrophin |
|  | calpain p94 |
|  | skeletal alpha-actin |
|  | fast troponin 1 |
| Skin | keratin K6 |
|  | keratin K1 |

TABLE 2-continued

Tissue-specific promoters

| Tissue | Promoter |
| --- | --- |
| Lung | CFTR |
|  | human cytokeratin 18 (K18) |
|  | pulmonary surfactant proteins A, B and C |
|  | CC-10 |
|  | P1 |
| Smooth muscle | sm22 alpha |
|  | SM-alpha-actin |
| Endothelium | endothelin-1 |
|  | E-selectin |
|  | von Willebrand factor |
|  | TIE (Korhonen et al., 1995) |
|  | KDR/flk-1 |
| Melanocytes | tyrosinase |
| Adipose tissue | lipoprotein lipase (Zechner et al., 1988) |
|  | adipsin (Spiegelman et al., 1989) |
|  | acetyl-CoA carboxylase (Pape and Kim, 1989) |
|  | glycerophosphate dehydrogenase (Dani et al., 1989) |
|  | adipocyte P2 (Hunt et al., 1986) |
| Blood | β-globin |

In certain indications, it may be desirable to activate transcription at specific times after administration of the gene therapy vector. This may be done with such promoters as those that are hormone or cytokine regulatable. For example in gene therapy applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful in the present invention. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitrypsin, lipoprotein lipase (Zechner et al., 1988), angiotensinogen (Ron et al., 1991), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin.

It is envisioned that cell cycle regulatable promoters may be useful in the present invention. For example, in a bi-cistronic gene therapy vector, use of a strong CMV promoter to drive expression of a first gene such as p16 that arrests cells in the G1 phase could be followed by expression of a second gene such as p53 under the control of a promoter that is active in the G1 phase of the cell cycle, thus providing a "second hit" that would push the cell into apoptosis. Other promoters such as those of various cyclins, PCNA, galectin-3, E2F1, p53 and BRCA1 could be used.

Tumor-specific promoters such as osteocalcin, hypoxia-responsive element (HRE), MAGE-4, CEA, alpha-fetoprotein, GRP78/BiP and tyrosinase may also be used to regulate gene expression in tumor endothelial cells. Other promoters that could be used according to the present invention include Lac-regulatable, chemotherapy inducible (e.g. MDR), and heat (hyperthermia) inducible promoters, Radiation-inducible (e.g., EGR (Joki et al., 1995)), Alphainhibin, RNA pol III tRNA met and other amino acid promoters, U1 snRNA (Bartlett et al., 1996), MC-1, PGK, -actin and alpha-globin. Many other promoters that may be useful are listed in Walther and Stein (1996).

It is envisioned that any of the above promoters alone or in combination with another may be useful according to the present invention depending on the action desired. In addition, this list of promoters is should not be construed to be exhaustive or limiting, those of skill in the art will know of other promoters that may be used in conjunction with the promoters and methods disclosed herein.

b. Enhancers

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters additional to the tissue specific promoters listed above, cellular promoters/enhancers and inducible promoters/enhancers that could be used in combination with the nucleic acid encoding a gene of interest in an expression construct (Table 3 and Table 4). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 3

| ENHANCER |
|---|
| Immunoglobulin Heavy Chain |
| Immunoglobulin Light Chain |
| T-Cell Receptor |
| HLA DQ$_\alpha$ and DQ$_\beta$ |
| $\beta$-Interferon |
| Interleukin-2 |
| Interleukin-2 Receptor |
| MHC Class II 5 |
| MHC Class II HLA-DR$_\alpha$ |
| $\beta$-Actin |
| Muscle Creatine Kinase |
| Prealbumin (Transthyretin) |
| Elastase I |
| Metallothionein |
| Collagenase |
| Albumin Gene |
| $\alpha$-Fetoprotein |
| $_\tau$-Globin |
| $\beta$-Globin |
| c-fos |
| c-HA-ras |
| Insulin |
| Neural Cell Adhesion Molecule (NCAM) |
| $\alpha$1-Antitrypsin |
| H2B (TH2B) Histone |
| Mouse or Type I Collagen |
| Glucose-Regulated Proteins (GRP94 and GRP78) |
| Rat Growth Hormone |

TABLE 3-continued

| ENHANCER |
|---|
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

TABLE 4

| Element | Inducer |
|---|---|
| MT II | Phorbol Ester (TPA) |
|  | Heavy metals |
| MMTV (mouse mammary tumor virus) | Glucocorticoids |
| $\beta$-Interferon | poly(rI)X |
|  | poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| $\alpha$-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | PMA |
| Thyroid Stimulating Hormone $_\alpha$ Gene | Thyroid Hormone |
| Insulin E Box | Glucose |

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

c. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

C. Protein Purification

In certain embodiments of the invention, inhibition of hyperproliferative cell growth, by administering to a cell a C-CAM1 cytoplasmic domain polypeptide, is contemplated. In other embodiments, the inhibition of angiogenesis is contemplated. In these embodiments, a subject is administered a C-CAM1 polypeptide to inhibit angiogenesis. In other embodiments, anti-hyperproliferative polypeptides can be adminsitered in combination with C-CAM1 polypeptides.

Thus, certain aspects of the present invention concern the purification, and in particular embodiments, the substantial purification, of a C-CAM1 or a C-CAM1 cytoplasmic domain protein that is encoded by the expression constructs described herein above. A C-CAM1 polypeptide may be administered as isolated and substantially purified protein in pharmaceutically acceptable formulations. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater -fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary. Angiostatin is a protein having a molecular weight of between approximately 38 kilodaltons and 45 kilodaltons as determined by reducing polyacrylamide gel electrophoresis (U.S. Pat. No. 5,733,876, specifically incorporated herein by reference).

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

D. Angiogenesis

One of the processes involved in the growth of both primary and secondary (metastatic) tumors is neovascularization, or creation of new blood vessels which grow into the tumor. This neovascularization is termed angiogenesis (Folkman, 1986; Folkman, 1989), which provides the growing tumor with a blood supply and essential nutrients. Although tumors of 1–2 mm in diameter can receive all nutrients by diffusion, further growth depends on the development of an adequate blood supply through angiogenesis. Inhibition of angiogenesis provides a novel and more general approach for treating both primary and secondary tumors by manipulation of the host microenvironment. The present invention contemplates the inhibition of angiogenesis by administering to a subject a C-CAM1 polypeptide or an expression construct encoding a C-CAM1 polypeptide.

The induction of angiogenesis is mediated by several angiogenic molecules released by tumor cells, tumor associated endothelial cells and the normal cells surrounding the tumor endothelial cells. The prevascular stage of a tumor is associated with local benign tumors, whereas the vascular stage is associated with tumors capable of metastasizing. Moreover, studies using light microscopy and immunohistochemistry concluded that the number and density of microvessels in different human cancers directly correlate with their potential to invade and produce metastasis (Weidner et al., 1991, 1993). Not all angiogenic tumors produce metastasis, but the inhibition of angiogenesis prevents the growth of tumor endothelial cells at both the primary and secondary sites and thus can prevent the emergence of metastases.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent and unregulated angiogenesis is characteristic of tumor growth and it supports the pathological damage seen in these cancer. Thus, tumor growth is an angiogenesis-dependent process (Folkman, 1971). After an initial prevascular phase, every increase in tumor endothelial cell population is preceded by an increase in new capillaries converging on the tumor. Expansion of tumor volume beyond this phase requires the induction of new capillary blood vessels.

Thus, inhibition of angiogenesis with C-CAMs would provide a novel and more general approach for treating both primary and secondary tumors than current anti-tumor therapies which target only the hyperproliferative tumor cells.

E. Methods of Gene Transfer

In order to mediate the effect transgene expression in a cell, it will be necessary to transfer the therapeutic expression constructs of the present invention into a cell. Such transfer may employ viral or non-viral methods of gene transfer. This section provides a discussion of methods and compositions of gene transfer.

1. Viral Vector-Mediated Transfer

The therapeutic genes are incorporated into a viral infectious particle to mediate gene transfer to a cell. Additional expression constructs encoding other therapeutic agents as described herein may also be transferred via viral transduction using infectious viral particles, for example, by transformation with an adenovirus vector of the present invention as described herein below. Alternatively, retroviral or bovine papilloma virus may be employed, both of which permit permanent transformation of a host cell with a gene(s) of interest. Thus, in one example, viral infection of cells is used in order to deliver therapeutically significant genes to a cell. Typically, the virus simply will be exposed to the appropriate host cell under physiologic conditions, permitting uptake of the virus. The present methods may be advantageously employed using a number of viral vectors, as discussed below.

Adenovirus. Adenovirus is particularly suitable for use as a gene transfer vector because of its mid-sized DNA genome, ease of manipulation, high titer, wide target-cell range, and high infectivity. The roughly 36 kB viral genome is bounded by 100–200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present invention, it is possible achieve both these goals while retaining the ability to manipulate the therapeutic constructs with relative ease.

The large displacement of DNA is possible because the cis elements required for viral DNA replication all are localized in the inverted terminal repeats (ITR) (100–200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194–385 bp (0.5–1.1 map units) at the left end of the viral genome (Hearing et al., 1987). This signal mimics the protein recognition site in bacteriophage X DNA where a specific sequence close to the left end, but outside the cohesive end sequence, mediates the binding to proteins that are required for insertion of the DNA into the head structure. E1 substitution vectors of Ad have demonstrated that a 450 bp (0–1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194–358 bp) region of the genome grew poorly even in a cell line that complemented the early (E1A) function (Hearing and Shenk, 1983). When a compensating adenoviral DNA (0–353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals are packaged selectively when compared to the helpers. If the preference is great enough, stocks approaching homogeneity should be achieved.

Retrovirus. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing a human cDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., 1975).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

Adeno-associated Virus. AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al. 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, 1996 ; Chatterjee et al., 1995; Ferrari et al., 1996; Fisher et al., 1996; Flotte et al., 1993; Goodman et al., 1994; Kaplitt et al., 1994; 1996, Kessler et al., 1996; Koeberl et al., 1997; Mizukami et al., 1996; Xiao et al., 1996).

AAV-mediated efficient gene transfer and expression in the lung has led to clinical trials for the treatment of cystic fibrosis (Carter and Flotte, 1996; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al., 1996).

Other Viral Vectors. Other viral vectors may be employed as expression constructs in the present invention. Vectors derived from viruses such as vaccinia virus (Ridgeway, 1988; Baichwal and Sugden, 1986; Coupar et al., 1988) canary pox virus, and herpes viruses may be employed. These viruses offer several features for use in gene transfer into various mammalian cells.

2. Non-viral Transfer

DNA constructs of the present invention are generally delivered to a cell, in certain situations, the nucleic acid to be transferred is non-infectious, and can be transferred using non-viral methods.

Several non-viral methods for the transfer of expression constructs into cultured mammalian cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene therapy.

Liposome-mediated nucleic acid delivery and expression of foreign DNA in vitro has been very successful. Using the β-lactamase gene, Wong et al. (1980) demonstrated the feasibility of liposome-mediated delivery and expression of foreign DNA in cultured chick embryo, HeLa, and hepatoma cells. Nicolau et al. (1987) accomplished successful liposome-mediated gene transfer in rats after intravenous injection. Also included are various commercial approaches involving "lipofection" technology.

Recent advances in lipid formulations have improved the efficiency of gene transfer in vivo (Templeton et al. 1997; WO 98/07408). A novel lipid formulation composed of an equimolar ratio of 1,2-bis(oleoyloxy)-3-(trimethyl ammonio)propane (DOTAP) and cholesterol significantly enhances systemic in vivo gene transfer, approximately 150-fold. The DOTAP:cholesterol lipid formulation forms unique structure termed a "sandwich liposome". This formulation is reported to "sandwich" DNA between an invaginated bilayer or "vase" structure. Beneficial characteristics of these lipid structures include a positive to negative charge or p, colloidal stabilization by cholesterol, two dimensional DNA packing and increased serum stability. Other formulations are well known, for example in U.S. Pat. No. 6,008,202, which is incorporated by reference.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

There are numerous U.S. Patent references describing pharmaceutical delivery employing liposomes. For example, U.S. Pat. No. 5,762,904, incorporated herein by reference, describes the use of polymerized liposomes, methods of preparing the polymerized liposomes and incorporating biologically active substances within the polymerized liposomes, and methods of administering polymerized liposomes containing a biologically active substance to be delivered to a patient are discussed. Additional polymerized vesicles are further described in U.S. Pat. No. 4,587,055 specifically incorporated herein by reference. Viral liposome particles are described in detail in U.S. Pat. No. 4,201,767, specifically incorporated herein by reference.

U.S. Pat. No. 5,759,566 is incorporated herein by reference and describes liposomic dispersions containing proteinaceous substances, that allow the systemic, local or topical administration of drugs by transmucosal route are described. This type of administration is specifically contemplated for use herein. In another embodiments, liposome-nucleic acid complexes for delivery via aerosol with the subsequent in viva expression of a protein encoded by the delivered gene are also contemplated. Such aerosolization provides a convenient method for treating pulmonary disorders, as well as for delivering substances systemically via the lung and are described in greater detail in U.S. Pat. No. 5,756,353, specifically incorporated herein by reference. The patents discussed above are presented merely by way of examples of the use of liposomes for delivery of nucleic acids, proteins or other therapeutic composition. There are numerous other U.S. Patents that describe the use of liposomes for a therapeutic delivery, as such the use of liposomal delivery of the nucleic acid and or protein compositions of the present invention are well within the skill of the art.

Other vector delivery systems which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferring (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor endothelial cells, by any number of receptor-ligand systems with or without liposomes. For example, the human prostate-specific antigen (Watt et al., 1986) may be used as the receptor for mediated delivery of a nucleic acid in prostate tissue.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM may also be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads F. Pharmaceuticals and Methods of Treating Cancer In a particular aspect, the present invention provides methods for inhibiting angiogenesis and the treatment of hyperproliferative diseases. Treatment methods will involve treating an individual with an effective amount of a C-CAM1 or C-CAM1 cytoplasmic domain protein. A C-CAM1 or C-CAM1 cytoplasmic domain may be provided as isolated and substantially purified protein in pharmaceutically acceptable formulations using formulation methods known to those of ordinary skill in the art. These formulations can be administered by standard routes. In general, the combinations may be administered by the topical, transdermal, dircet intratumoral, intraperitoneal, oral, rectal or parenteral (e.g., intravenous, subcutaneous or intramuscular) administration. In addition, a C-CAM1 or C-CAM1 cytoplasmic domain may be incorporated into biodegradable polymers allowing for sustained release of the compound, the polymers being implanted in the vicinity of where drug delivery is desired, for example, at the site of a tumor or implanted so that a C-CAM1 or C-CAM1 cytoplasmic domain is slowly released systemically.

In an alternative embodiment, a C-CAM1 or C-CAM1 cytoplasmic domain may be provided as a protein composition for example in an aqueous solution or as a liposomal complex. The discussion of liposomes as delivery vehicles presented above for nucleic acid constructs is equally applicable to delivery of protein or other drug compositions. Further, a C-CAM1 or C-CAM1 cytoplasmic domain protein may be provided as described above in a viral expression construct containing a gene that encodes a C-CAM1 or C-CAM1 cytoplasmic domain. An effective amount is described, generally, as that amount sufficient to detectably and repeatedly to ameliorate, reduce, minimize or limit the extent of a disease or its symptoms. More rigorous definitions may apply, including elimination, eradication or cure of disease. In the context of the present invention, the diseases include hyperproliferative diseases, such as cancer, and extend into affecting conditions that alter the progression of the disease, for example, angiogenesis and/or the effect of inhibiting angeiogenesis on tumor growth.

To kill cells, inhibit cell growth, inhibit metastasis, decrease tumor size and otherwise reverse or reduce the malignant phenotype of tumor endothelial cells, using the methods and compositions of the present invention, one would generally contact a "target" cell with the therapeutic expression construct. This may be combined with compositions comprising other agents effective in the treatment of cancer. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent.

Alternatively, the gene therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 h of each other and, more preferably, within about 6–12 h of each other, with a delay time of only about 12 h being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described gene therapy.

Where clinical application of a gene therapy is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the compound, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

The compositions of the present invention may include classic pharmaceutical preparations. Dispersions also can be prepared in glycerol, liquid polyethylene glycols, and mixtures thereof and in oils. Under ordinary conditions of storage and use, these preparations contain a preservative to prevent the growth of microorganisms.

Depending on the particular cancer to be treated, administration of therapeutic compositions according to the present invention will be via any common route so long as the target tissue is available via that route. This includes oral, nasal, buccal, rectal, vaginal or topical. Topical administration would be particularly advantageous for treatment of skin cancers. Alternatively, administration will be by orthotopic, intradermal, subcutaneous, intramuscular, intraperitoneal or intravenous injection. Such compositions would normally be administered as pharmaceutically acceptable compositions that include physiologically acceptable carriers, buffers or other excipients.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

The treatments may include various "unit doses." Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time. Unit dose of the present invention may conveniently may be described in terms of plaque forming units (pfu) of the viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher.

Preferably, patients will have adequate bone marrow function (defined as a peripheral absolute granulocyte count of >2,000/mm$^3$ and a platelet count of 100,000/mm$^3$), adequate liver function (bilirubin <1.5 mg/dl) and adequate renal function (creatinine <1.5 mg/dl).

1. Gene Therapy

One embodiment of the present invention involves the use of vectors, including viral vectors, to deliver therapeutic genes to cancer and other hyperproliferative cells. Target cancer cells include cancers of the lung, brain, prostate, kidney, liver, ovary, breast, skin, stomach, esophagus, head and neck, testicles, colon, cervix, lymphatic system and blood.

The present invention contemplates the use of a variety of different genes in combination with C-CAM1 cytoplasmic domain constructs. For example, genes encoding enzymes, hormones, cytokines, oncogenes, receptors, tumor suppressors, transcription factors, drug selectable markers, toxins and various antigens are contemplated as suitable genes for use according to the present invention. In addition, antisense constructs derived from oncogenes are other "genes" of interest according to the present invention. The following are genes contemplated for use in the present invention.

a. Tumor Suppressors p53. p53 currently is recognized as a tumor suppressor gene. High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently-mutated gene in common human cancers. It is mutated in over 50% of human NSCLC (Hollstein et al., 1991) and in a wide spectrum of other tumors.

Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

p53 appears dominant over the mutant gene and will select against proliferation when transfected into cells with the mutant gene. Normal expression of the transfected p53 does not affect the growth of cells with endogenous p53. Thus, such constructs might be taken up by normal cells without adverse effects. It is thus proposed that the treatment of p53-associated cancers with wild-type p53 or other therapies described herein will reduce the number of malignant cells or their growth rate, alternatively the treatment will result in the decrease of the metastatic potential of the cancer cell, a decrease in tumor size or a halt in the growth the tumor.

p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the $p16^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyper-phosphorylation of the Rb protein. p16 also is known to regulate the function of CDK6.

Additional Tumor Suppressors. Other tumor suppressors that may be employed according to the present invention include RB, APC, DCC, NF-1, NF-2, WT-1, MEN-I, MEN-II, zac1, p73, VHL, MMAC1, FCC and MCC. Additional inducers of apoptosis including members of the Bcl-2 family such as Bax, Bak, Bim, Bik, Bid, Bad, or Harakiri gene, as well as Ad E1B and ICE-CED3 proteases, similarly could find use according to the present invention.

b. Enzymes

Various enzyme genes are of interest according to the present invention. Such enzymes include cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase and human thymidine kinase.

c. Cytokines

Other classes of genes that are contemplated to be inserted into the therapeutic expression constructs of the present invention include interleukins and cytokines. Interleukin 1 (IL-1), IL-2, IL-3, IL-4, IL-5, IL-6, IL-7, IL-8, IL-9, IL-10, IL-11 IL-12, GM-CSF and G-CSF.

d. Antibodies

In yet another embodiment, the heterologous gene may include a single-chain antibody. Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule.

Single-chain antibody variable fragments (Fvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody.

Antibodies to a wide variety of molecules can be used in combination with the present invention, including antibodies against oncogenes, toxins, hormones, enzymes, viral or bacterial antigens, transcription factors, receptors and the like.

e. Antisense constructs

Oncogenes such as ras, myc, neu, raf erb, src, fins, jun, trk, ret, gsp, hst, bcl-2, Bcl-$x_L$ and abl also are suitable targets. However, for therapeutic benefit, these oncogenes would be expressed as an antisense nucleic acid, so as to inhibit the expression of the oncogene. The term "antisense nucleic acid" is intended to refer to the oligonucleotides complementary to the base sequences of oncogene-encoding DNA and RNA. Antisense oligonucleotides, when introduced into a target cell, specifically bind to their target nucleic acid and interfere with transcription, RNA processing, transport and/or translation. Targeting double-stranded (ds) DNA with oligonucleotide leads to triple-helix formation; targeting RNA will lead to double-helix formation.

Antisense constructs may be designed to bind to the promoter and other control regions, exons, introns or even exon-intron boundaries of a gene. Antisense RNA constructs, or DNA encoding such antisense RNAs, may be employed to inhibit gene transcription or translation or both within a host cell, either in vitro or in vivo, such as within a host animal, including a human subject. Nucleic acid sequences comprising "complementary nucleotides" are those which are capable of base-pairing according to the standard Watson-Crick complementary rules. That is, that the larger purines will base pair with the smaller pyrimidines to form only combinations of guanine paired with cytosine (G:C) and adenine paired with either thymine (A:T), in the case of DNA, or adenine paired with uracil (A:U) in the case of RNA.

As used herein, the terms "complementary" or "antisense sequences" mean nucleic acid sequences that are substantially complementary over their entire length and have very few base mismatches. For example, nucleic acid sequences of fifteen bases in length may be termed complementary when they have a complementary nucleotide at thirteen or fourteen positions with only single or double mismatches. Naturally, nucleic acid sequences which are "completely complementary" will be nucleic acid sequences which are entirely complementary throughout their entire length and have no base mismatches.

While all or part of the gene sequence may be employed in the context of antisense construction, statistically, any sequence 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

f. Ribozyme constructs

As an alternative to targeted antisense delivery, targeted ribozymes may be used. The term "ribozyme" refers to an RNA-based enzyme capable of targeting and cleaving particular base sequences in oncogene DNA and RNA. Ribozymes either can be targeted directly to cells, in the form of RNA oligo-nucleotides incorporating ribozyme sequences, or introduced into the cell as an expression construct encoding the desired ribozymal RNA. Ribozymes may be used and applied in much the same way as described for antisense nucleic acids.

g. Selectable Markers

In certain embodiments of the invention, the therapeutic expression constructs of the present invention contain nucleic acid constructs whose expression may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as herpes simplex virus thymidine kinase (tk) may be employed. Immunologic markers also can be employed. The selectable marker employed is not believed to be important, so long as it is capable of being expressed simultaneously with the nucleic acid encoding a gene product. Further examples of selectable markers are well known to one of skill in the art and include reporters such as EGFP, β-gal or chloramphenicol acetyltransferase (CAT).

h. Multigene Constructs and IRES

In certain embodiments of the invention, the use of internal ribosome binding sites (IRES) elements are used to create multigene polycistronic messages. IRES elements are able to bypass the ribosome scanning model of 5'-methylated, Cap-dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

According to the present invention, one may treat the cancer by directly injection a tumor with a viral vector. Alternatively, the tumor may be infused or perfused with a vector using any suitable delivery vehicle. Local or regional administration, with respect to the tumor, also is contemplated. Finally, systemic administration may be performed. Continuous administration also may be applied where appropriate, for example, where a tumor is excised and the tumor bed is treated to eliminate residual, microscopic disease. Delivery via syringe or catherization is preferred. Such continuous perfusion may take place for a period from about 15 minutes to about 30 minutes, to about 1–2 hours, to about 2–6 hours, to about 6–12 hours, to about 12–24 hours, to about 1–2 days, to about 1–2 wk or longer following the initiation of treatment. Generally, the dose of the therapeutic composition via continuous perfusion will be equivalent to that given by a single or multiple injections, adjusted over a period of time during which the perfusion occurs.

For tumors of >4 cm, the volume to be administered will be about 4–10 ml (preferably 10 ml), while for tumors of <4 cm, a volume of about 1–3 ml will be used (preferably 3 ml). Multiple injections of the C-CAM1 or C-CAM1 cytoplasmic domain based therapy may be delivered as single dose comprise about 0.1 to about 0.5 ml volumes. The viral particles may advantageously be contacted by administering multiple injections to the tumor, spaced at approximately 1 cm intervals.

In certain embodiments, the tumor being treated may not, at least initially, be resectable. Treatments with therapeutic viral constructs may increase the resectability of the tumor due to shrinkage at the margins or by elimination of certain particularly invasive portions. Following treatments, resection may be possible. Additional viral treatments subsequent to resection will serve to eliminate microscopic residual disease at the tumor site.

A typical course of treatment, for a primary tumor or a post-excision tumor bed, will involve multiple doses of a C-CAM1 or C-CAM1 cytoplasmic domain for antiangiogenic therapy followed by cancer therapy.

2. Radiotherapy

In other embodiments, the inhibition of cell hyperproliferation is combined with radiotherapy. The radiation therapy used herein includes the use of γ-rays, X-rays, and/or the directed delivery of radioisotopes to tumor endothelial cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Chemotherapy

In still further embodiments of the invention, a therapeutic construct encoding C-CAM1 or a C-CAM1 polypeptide may be administered as an anti-hyperproliferative therapy (therapy targeting hyperproliferation in order to suppress, reduce, inhibit, amerliorate, or prevent hyperproliferation of a cell) in conjunction with chemotherapy, another anti-hyperproliferative therapy. Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, TAXOL (paclitaxel), transplatinum, 5-fluorouracil, vincristine, vinilastine and methotrexate or any analog or derivative variant thereof. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, corticosteroid hormones, mitotic inhibitors, and nitrosoureas, and any analog or derivative variant thereof. It is contemplated that the nucleic acid formulations described herein can be used in combination with one or more of these agents according to the present invention.

a. Alkylating agents

Alkylating agents are drugs that directly interact with genomic DNA to prevent the cancer cell from proliferating. This category of chemotherapeutic drugs represents agents that affect all phases of the cell cycle, that is, they are not phase-specific. Alkylating agents can be implemented to treat chronic leukemia, non-Hodgkin's lymphoma, Hodgkin's disease, multiple myeloma, and particular cancers of the breast, lung, and ovary. They include: busulfan, chlorambucil, cisplatin, cyclophosphamide (CYTOXAN), dacarbazine, ifosfamide, mechlorethamine (MUSTARGEN), and melphalan. Troglitazaone can be used to treat cancer in combination with any one or more of these alkylating agents, some of which are discussed below.

i. Busulfan

Busulfan (also known as MYLERAN) is a bifunctional alkylating agent. Busulfan is known chemically as 1,4-butanediol dimethanesulfonate.

Busulfan is not a structural analog of the nitrogen mustards. Busulfan is available in tablet form for oral administration. Each scored tablet contains 2 mg busulfan and the inactive ingredients magnesium stearate and sodium chloride.

Busulfan is indicated for the palliative treatment of chronic myelogenous (myeloid, myelocytic, granulocytic) leukemia. Although not curative, busulfan reduces the total granulocyte mass, relieves symptoms of the disease, and improves the clinical state of the patient. Approximately 90% of adults with previously untreated chronic myelogenous leukemia will obtain hematologic remission with regression or stabilization of organomegaly following the use of busulfan. It has been shown to be superior to splenic irradiation with respect to survival times and maintenance of hemoglobin levels, and to be equivalent to irradiation at controlling splenomegaly.

ii. Chlorambucil

Chlorambucil (also known as LEUKERAN) is a bifunctional alkylating agent of the nitrogen mustard type that has been found active against selected human neoplastic diseases. Chlorambucil is known chemically as 4-[bis(2-chlorethyl)amino] benzenebutanoic acid.

Chlorambucil is available in tablet form for oral administration. It is rapidly and completely absorbed from the gastrointestinal tract. After single oral doses of 0.6–1.2 mg/kg, peak plasma chlorambucil levels are reached within one hour and the terminal half-life of the parent drug is estimated at 1.5 hours. 0.1 to 0.2 mg/kg/day or 3 to 6 mg/m$^2$/day or alternatively 0.4 mg/kg may be used for antineoplastic treatment. Treatment regimes are well know to those of skill in the art and can be found in the "Physicians Desk Reference" and in "Remington's Pharmaceutical Sciences" referenced herein.

Chlorambucil is indicated in the treatment of chronic lymphatic (lymphocytic) leukemia, malignant lymphomas including lymphosarcoma, giant follicular lymphoma and Hodgkin's disease. It is not curative in any of these disorders but may produce clinically useful palliation.

iii. Cisplatin

Cisplatin has been widely used to treat cancers such as metastatic testicular or ovarian carcinoma, advanced bladder cancer, head or neck cancer, cervical cancer, lung cancer or other tumors. Cisplatin can be used alone or in combination with other agents, with efficacious doses used in clinical applications of 15–20 mg/M$^2$ for 5 days every three weeks for a total of three courses. Exemplary doses may be 0.50 mg/M$^2$, 1.0 mg/m$^2$, 1.50 mg/m$^2$, 1.75 mg/m$^2$, 2.0 mg/m$^2$, 3.0 mg/m$^2$, 4.0 mg/m$^2$, 5.0 mg/$^2$, 10 mg//m$^2$. Of course, all of these dosages are exemplary, and any dosage in-between these points is also expected to be of use in the invention.

Cisplatin is not absorbed orally and must therefore be delivered via injection intravenously, subcutaneously, intratumorally or intraperitoneally.

iv. Cyclophosphamide

Cyclophosphamide is 2H-1,3,2-Oxazaphosphorin-2-amine, N,N-bis(2-chloroethyl)tetrahydro-, 2-oxide, monohydrate; termed Cytoxan available from Mead Johnson; and Neosar available from Adria. Cyclophosphamide is prepared by condensing 3-amino-1-propanol with N,N-bis(2-chlorethyl) phosphoramidic dichloride [(ClCH$_2$CH$_2$)$_2$N--POCl$_2$] in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parental routes and does not cause local vesication, necrosis, phlebitis or even pain.

Suitable doses for adults include, orally, 1 to 5 mg/kg/day (usually in combination), depending upon gastrointestinal tolerance; or 1 to 2 mg/kg/day; intravenously, initially 40 to 50 mg/kg in divided doses over a period of 2 to 5 days or 10 to 15 mg/kg every 7 to 10 days or 3 to 5 mg/kg twice a week or 1.5 to 3 mg/kg/day. A dose 250 mg/kg/day may be administered as an antineoplastic. Because of gastrointestinal adverse effects, the intravenous route is preferred for loading. During maintenance, a leukocyte count of 3000 to 4000/mm$^3$ usually is desired. The drug also sometimes is administered intramuscularly, by infiltration or into body cavities. It is available in dosage forms for injection of 100, 200 and 500 mg, and tablets of 25 and 50 mg the skilled artisan is referred to "Remington's Pharmaceutical Sciences" 15th Edition, chapter 61, incorporate herein as a reference, for details on doses for administration.

v. Melphalan

Melphalan, also known as ALKERAN, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. It is known chemically as 4-[bis(2-chloroethyl)amino]-L-phenylalanine.

Melphalan is the active L-isomer of the compound and was first synthesized in 1953 by Bergel and Stock; the D-isomer, known as medphalan, is less active against certain animal tumors, and the dose needed to produce effects on chromosomes is larger than that required with the L-isomer. The racemic (DL-) form is known as merphalan or sarcolysin. Melphalan is insoluble in water and has a $pKa_1$ of ~2.1. Melphalan is available in tablet form for oral administration and has been used to treat multiple myeloma.

Available evidence suggests that about one third to one half of the patients with multiple myeloma show a favorable response to oral administration of the drug.

Melphalan has been used in the treatment of epithelial ovarian carcinoma. One commonly employed regimen for the treatment of ovarian carcinoma has been to administer melphalan at a dose of 0.2 mg/kg daily for five days as a single course. Courses are repeated every four to five weeks depending upon hematologic tolerance (Smith and Rutledge, 1975; Young et al., 1978). Alternatively the dose of melphalan used could be as low as 0.05 mg/kg/day or as high as 3 mg/kg/day or any dose in between these doses or above these doses. Some variation in dosage will necessarily occur depending on the condition of the subject being treated. The person responsible for administration will, in any event, determine the appropriate dose for the individual subject b. Antimetabolites Antimetabolites disrupt DNA and RNA synthesis. Unlike alkylating agents, they specifically influence the cell cycle during S phase. They have used to combat chronic leukemias in addition to tumors of breast, ovary and the gastrointestinal tract. Antimetabolites include 5-fluorouracil (5-FU), cytarabine (Ara-C), fludarabine, gemcitabine, and methotrexate.

i. 5-Fluorouracil

5-Fluorouracil (5-FU) has the chemical name of 5-fluoro-2,4(1H,3H)-pyrimidinedione. Its mechanism of action is thought to be by blocking the methylation reaction of deoxyuridylic acid to thymidylic acid. Thus, 5-FU interferes with the syntheisis of deoxyribonucleic acid (DNA) and to a lesser extent inhibits the formation of ribonucleic acid (RNA). Since DNA and RNA are essential for cell division and proliferation, it is thought that the effect of 5-FU is to create a thymidine deficiency leading to cell death. Thus, the effect of 5-FU is found in cells that rapidly divide, a characteristic of metastatic cancers.

c. Antitumor Antibiotics

Antitumor antibiotics have both antimicrobial and cytotoxic activity. These drugs also interfere with DNA by chemically inhibiting enzymes and mitosis or altering cellular membranes. These agents are not phase specific so they work in all phases of the cell cycle. Thus, they are widely used for a variety of cancers. Examples of antitumor antibiotics include bleomycin, dactinomycin, daunorubicin, doxorubicin (ADRIAMYCIN), and idarubicin, some of which are discussed in more detail below. Widely used in clinical setting for the treatment of neoplasms these compounds are administered through bolus injections intravenously at doses ranging from 25–75 mg/m$^2$ at 21 day intervals for adriamycin, to 35–100 mg/m$^2$ for etoposide intravenously or orally.

i. Doxorubicin

Doxorubicin hydrochloride, 5,12-Naphthacenedione, (8s-cis)-10-[(3-amino-2,3,6-trideoxy-a-L-lyxo-hexopyranosyl) oxy]-7,8,9,10-tetrahydro-6,8,11-trihydroxy-8-(hydroxyacetyl)-1-methoxy-hydrochloride (hydroxydaunorubicin hydrochloride, ADRIAMYCIN) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of ovarian, endometrial and breast tumors, bronchogenic oat-cell carcinoma, non-small cell lung carcinoma, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma soft tissue sarcoma, Ewing's sarcoma, rhabdomyosarcoma and acute lymphocytic leukemia. It is an alternative drug for the treatment of islet cell, cervical, testicular and adrenocortical cancers. It is also an immunosuppressant.

Doxorubicin is absorbed poorly and must be administered intravenously. The pharmacokinetics are multicompartmental. Distribution phases have half-lives of 12 minutes and 3.3 hr. The elimination half-life is about 30 hr. Forty to 50% is secreted into the bile. Most of the remainder is metabolized in the liver, partly to an active metabolite (doxorubicinol), but a few percent is excreted into the urine. In the presence of liver impairment, the dose should be reduced.

Appropriate doses are, intravenous, adult, 60 to 75 mg/m$^2$ at 21-day intervals or 25 to 30 mg/m$^2$ on each of 2 or 3 successive days repeated at 3- or 4-wk intervals or 20 mg/m$^2$ once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/m$^2$ in patients with normal heart function and 400 mg/m$^2$ in persons having received mediastinal irradiation. Alternatively, 30 mg/m$^2$ on each of 3 consecutive days, repeated every 4 wk. Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

ii. Daunorubicin

Daunorubicin hydrochloride, 5,12-Naphthacenedione, (8S-cis)-8-acetyl-10-[(3-amino-2,3,6-trideoxy-a-L-lyxo-hexanopyranosyl)oxy]-7,8,9,10-tetrahydro-6,8,11-trihydroxy-10-methoxy-, hydrochloride; also termed CERUBIDINE and available from Wyeth. Daunorubicin intercalates into DNA, blocks DNA directed RNA polymerase and inhibits DNA synthesis. It can prevent cell division in doses that do not interfere with nucleic acid synthesis.

In combination with other drugs it is included in the first-choice chemotherapy of acute myelocytic leukemia in adults (for induction of remission), acute lymphocytic leukemia and the acute phase of chronic myelocytic leukemia. Oral absorption is poor, and it must be given intravenously. The half-life of distribution is 45 minutes and of elimination, about 19 hr. The half-life of its active metabolite, daunorubicinol, is about 27 hr. Daunorubicin is metabolized mostly in the liver and also secreted into the bile (ca 40%). Dosage must be reduced in liver or renal insufficiencies.

Suitable doses are (base equivalent), intravenous adult, younger than 60 yr. 45 mg/m$^2$/day (30 mg/m$^2$ for patients older than 60 yr.) for 1, 2 or 3 days every 3 or 4 wk or 0.8 mg/kg/day for 3 to 6 days every 3 or 4 wk; no more than 550 mg/m$^2$ should be given in a lifetime, except only 450 mg/m$^2$ if there has been chest irradiation; children, 25 mg/m$^2$ once a week unless the age is less than 2 yr. or the body surface less than 0.5 m, in which case the weight-based adult schedule is used. It is available in injectable dosage forms (base equivalent) 20 mg (as the base equivalent to 21.4 mg of the hydrochloride). Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

iii. Mitomycin

Mitomycin (also known as MUTAMYCIN and/or mitomycin-C) is an antibiotic isolated from the broth of *Streptomyces caespitosus* which has been shown to have antitumor activity. The compound is heat stable, has a high melting point, and is freely soluble in organic solvents.

Mitomycin selectively inhibits the synthesis of deoxyribonucleic acid (DNA). The guanine and cytosine content correlates with the degree of mitomycin-induced cross-linking. At high concentrations of the drug, cellular RNA and protein synthesis are also suppressed.

In humans, mitomycin is rapidly cleared from the serum after intravenous administration. Time required to reduce the serum concentration by 50% after a 30 mg. bolus injection is 17 minutes. After injection of 30 mg, 20 mg, or 10 mg I.V., the maximal serum concentrations were 2.4 mg/mL, 1.7 mg/mL, and 0.52 mg/mL, respectively. Clearance is effected primarily by metabolism in the liver, but metabolism occurs in other tissues as well. The rate of clearance is inversely proportional to the maximal serum concentration because, it is thought, of saturation of the degradative pathways. Approximately 10% of a dose of mitomycin is excreted unchanged in the urine. Since metabolic pathways are saturated at relatively low doses, the percent of a dose excreted in urine increases with increasing dose. In children, excretion of intravenously administered mitomycin is similar.

iv. Actinomycin D

Actinomycin D (Dactinomycin) [50-76-0]; $C_{62}H_{86}N_{12}O_{16}$ (1255.43) is an antineoplastic drug that inhibits DNA-dependent RNA polymerase. It is a component of first-choice combinations for treatment of choriocarcinoma, embryonal rhabdomyosarcoma, testicular tumor and Wilms' tumor. Tumors that fail to respond to systemic treatment sometimes respond to local perfusion. Dactinomycin potentiates radiotherapy. It is a secondary (efferent) immunosuppressive.

Actinomycin D is used in combination with primary surgery, radiotherapy, and other drugs, particularly vincristine and cyclophosphamide. Antineoplastic activity has also been noted in Ewing's tumor, Kaposi's sarcoma, and soft-tissue sarcomas. Dactinomycin can be effective in women with advanced cases of choriocarcinoma. It also produces consistent responses in combination with chlorambucil and methotrexate in patients with metastatic testicular carcinomas. A response may sometimes be observed in patients with Hodgkin's disease and non-Hodgkin's lymphomas. Dactinomycin has also been used to inhibit immunological responses, particularly the rejection of renal transplants.

Half of the dose is excreted intact into the bile and 10% into the urine; the half-life is about 36 hr. The drug does not pass the blood-brain barrier. Actinomycin D is supplied as a lyophilized powder (0/5 mg in each vial). The usual daily dose is 10 to 15 mg/kg; this is given intravenously for 5 days; if no manifestations of toxicity are encountered, additional courses may be given at intervals of 3 to 4 weeks. Daily injections of 100 to 400 mg have been given to children for 10 to 14 days; in other regimens, 3 to 6 mg/kg, for a total of 125 mg/kg, and weekly maintenance doses of 7.5 mg/kg have been used. Although it is safer to administer the drug into the tubing of an intravenous infusion, direct intravenous injections have been given, with the precaution of discarding the needle used to withdraw the drug from the vial in order to avoid subcutaneous reaction. Exemplary doses may be 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

v. Bleomycin

Bleomycin is a mixture of cytotoxic glycopeptide antibiotics isolated from a strain of *Streptomyces verticillus*. Although the exact mechanism of action of bleomycin is unknown, available evidence would seem to indicate that the main mode of action is the inhibition of DNA synthesis with some evidence of lesser inhibition of RNA and protein synthesis.

In mice, high concentrations of bleomycin are found in the skin, lungs, kidneys, peritoneum, and lymphatics. Tumor cells of the skin and lungs have been found to have high concentrations of bleomycin in contrast to the low concentrations found in hematopoietic tissue. The low concentrations of bleomycin found in bone marrow may be related to high levels of bleomycin degradative enzymes found in that tissue.

In patients with a creatinine clearance of >35 mL per minute, the serum or plasma terminal elimination half-life of bleomycin is approximately 115 minutes. In patients with a creatinine clearance of <35 mL per minute, the plasma or serum terminal elimination half-life increases exponentially as the creatinine clearance decreases. In humans, 60% to 70% of an administered dose is recovered in the urine as active bleomycin. Bleomycin may be given by the intramuscular, intravenous, or subcutaneous routes. It is freely soluble in water.

Bleomycin should be considered a palliative treatment. It has been shown to be useful in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), skin, penis, cervix, and vulva. It has also been used in the treatment of lymphomas and testicular carcinoma.

Because of the possibility of an anaphylactoid reaction, lymphoma patients should be treated with two units or less for the first two doses. If no acute reaction occurs, then the regular dosage schedule may be followed.

Improvement of Hodgkin's Disease and testicular tumors is prompt and noted within 2 weeks. If no improvement is seen by this time, improvement is unlikely. Squamous cell cancers respond more slowly, sometimes requiring as long as 3 weeks before any improvement is noted.

d. Corticosteroid Hormones

Corticosteroid hormones are useful in treating some types of cancer (lymphoma, leukemias, and multiple myeloma). Though these hormones have been used in the treatment of many non-cancer conditions, they are considered chemotherapy drugs when they are implemented to kill or slow the growth of cancer cells. Corticosteroid hormones can increase the effectiveness of other chemotherapy agents, and consequently, they are frequently used in combination treatments. Prednisone and dexamethasone are examples of corticosteroid hormones.

e. Mitotic Inhibitors

Mitotic inhibitors include plant alkaloids and other natural agents that can inhibit either protein synthesis required for cell division or mitosis. They operate during a specific phase during the cell cycle. Mitotic inhibitors comprise docetaxel, etoposide (VP16), paclitaxel, (TAXOL), vinblastine, vincristine, and vinorelbine.

i. Etoposide (VP16)

VP16 is also known as etoposide and is used primarily for treatment of testicular tumors, in combination with bleomycin and cisplatin, and in combination with cisplatin for small-cell carcinoma of the lung. It is also active against non-Hodgkin's lymphomas, acute nonlymphocytic leukemia, carcinoma of the breast, and Kaposi's sarcoma associated with acquired immunodeficiency syndrome (AIDS).

VP16 is available as a solution (20 mg/ml) for intravenous administration and as 50-mg, liquid-filled capsules for oral use. For small-cell carcinoma of the lung, the intravenous dose (in combination therapy) is can be as much as 100 mg/m$^2$ or as little as 2 mg/m$^2$, routinely 35 mg/m$^2$, daily for 4 days, to 50 mg/m$^2$, daily for 5 days have also been used. When given orally, the dose should be doubled. Hence the doses for small cell lung carcinoma may be as high as 200–250 mg/m$^2$. The intravenous dose for testicular cancer (in combination therapy) is 50 to 100 mg/m$^2$ daily for 5 days, or 100 mg/m$^2$ on alternate days, for three doses. Cycles of therapy are usually repeated every 3 to 4 weeks. The drug should be administered slowly during a 30- to 60-minute infusion in order to avoid hypotension and bronchospasm, which are probably due to the solvents used in the formulation.

ii. TAXOL

TAXOL is an experimental antimitotic agent, isolated from the bark of the ash tree, *Taxus brevifolia*. It binds to tubulin (at a site distinct from that used by the vinca alkaloids) and promotes the assembly of microtubules. TAXOL is currently being evaluated clinically; it has activity against malignant melanoma and carcinoma of the ovary. Maximal doses are 30 mg/m$^2$ per day for 5 days or 210 to 250 mg/m$^2$ given once every 3 weeks. Of course, all of these dosages are exemplary, and any dosage in-between these points is also expected to be of use in the invention.

iii. Vinblastine

Vinblastine is another example of a plant aklyloid that can be used in combination with gene therapy for the treatment of cancer and precancer. When cells are incubated with vinblastine, dissolution of the microtubules occurs.

Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes.

After intravenous injection, vinblastine has a multiphasic pattern of clearance from the plasma; after distribution, drug disappears from plasma with half-lives of approximately 1 and 20 hours. Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 mM).

Vinblastine sulfate is available in preparations for injection. The drug is given intravenously; special precautions must be taken against subcutaneous extravasation, since this may cause painful irritation and ulceration. The drug should not be injected into an extremity with impaired circulation. After a single dose of 0.3 mg/kg of body weight, myelosuppression reaches its maximum in 7 to 10 days. If a moderate level of leukopenia (approximately 3000 cells/mm$^3$) is not attained, the weekly dose may be increased gradually by increments of 0.05 mg/kg of body weight. In regimens designed to cure testicular cancer, vinblastine is used in doses of 0.3 mg/kg every 3 weeks irrespective of blood cell counts or toxicity.

The most important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, neuroblastoma, and Letterer-Siwe disease (histiocytosis X), as well as in carcinoma of the breast and choriocarcinoma in women.

Doses of vinblastine will be determined by the clinician according to the individual patients need. 0.1 to 0.3 mg/kg can be administered or 1.5 to 2 mg/m$^2$ can also be administered. Alternatively, 0.1 mg/m$^2$, 0.12 mg/m$^2$, 0.14 mg/m$^2$, 0.15 mg/m$^2$, 0.2 mg/m$^2$, 0.25 mg/m$^2$, 0.5 mg/m$^2$, 1.0 mg/m$^2$, 1.2 mg/m$^2$, 1.4 mg/m$^2$, 1.5 mg/m$^2$, 2.0 mg/m$^2$, 2.5 mg/m$^2$, 5.0 mg/m$^2$, 6 mg/m$^2$, 8 mg/m$^2$, 9 mg/m$^2$, 10 mg/m$^2$, can be given. Of course, all of these dosages are exemplary, and any dosage in-between these points is also expected to be of use in the invention.

iv. Vincristine

Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

The relatively low toxicity of vincristine for normal marrow cells and epithelial cells make this agent unusual among anti-neoplastic drugs, and it is often included in combination with other myelosuppressive agents.

Unpredictable absorption has been reported after oral administration of vinblastine or vincristine. At the usual clinical doses the peak concentration of each drug in plasma is approximately 0.4 mM.

Vinblastine and vincristine bind to plasma proteins. They are extensively concentrated in platelets and to a lesser extent in leukocytes and erythrocytes. Vincristine has a multiphasic pattern of clearance from the plasma; the terminal half-life is about 24 hours. The drug is metabolized in the liver, but no biologically active derivatives have been identified. Doses should be reduced in patients with hepatic dysfunction. At least a 50% reduction in dosage is indicated if the concentration of bilirubin in plasma is greater than 3 mg/dl (about 50 mM).

Vincristine sulfate is available as a solution (1 mg/ml) for intravenous injection. Vincristine used together with corticosteroids is presently the treatment of choice to induce remissions in childhood leukemia; the optimal dosages for these drugs appear to be vincristine, intravenously, 2 mg/mm$^2$ of body-surface area, weekly, and prednisone, orally, 40 mg/m$^2$, daily. Adult patients with Hodgkin's disease or non-Hodgkin's lymphomas usually receive vincristine as a part of a complex protocol. When used in the MOPP regimen, the recommended dose of vincristine is 1.4 mg/m$^2$. High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine has been effective in Hodgkin's disease and other lymphomas. Although it appears to be somewhat less beneficial than vinblastine when used alone in Hodgkin's disease, when used with mechlorethamine, prednisone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisone. Vincristine is more useful than vinblastine in lymphocytic leukemia. Beneficial response have been reported in patients with a variety of other neoplasms, particularly Wilms' tumor, neuroblastoma, brain tumors, rhabdomyosarcoma, and carcinomas of the breast, bladder, and the male and female reproductive systems.

Doses of vincristine for use will be determined by the clinician according to the individual patients need. 0.01 to 0.03 mg/kg or 0.4 to 1.4 mg/m$^2$ can be administered or 1.5 to 2 mg/m$^2$ can alos be administered. Alternatively 0.02 mg/m$^2$, 0.05 mg/m$^2$, 0.06 mg/m$^2$, 0.07 mg/m$^2$, 0.08 mg/m$^2$, 0.1 mg/m$^2$, 0.12 mg/m$^2$, 0.14 mg/m$^2$, 0.15 mg/m$^2$, 0.25 mg/m$^2$ can be given as a constant intravenous infusion. Of course, all of these dosages are exemplary, and any dosage in-between these points is also expected to be of use in the invention.

f. Nitrosureas

Nitrosureas, like alkylating agents, inhibit DNA repair proteins. They are used to treat non-Hodgkin's lymphomas, multiple myeloma, malignant melanoma, in addition to brain tumors. Examples include carmustine and lomustine.

a. Carmustine

Carmustine (sterile carmustine) is one of the nitrosoureas used in the treatment of certain neoplastic diseases. It is 1,3bis (2-chloroethyl)-1-nitrosourea. It is lyophilized pale yellow flakes or congealed mass with a molecular weight of 214.06. It is highly soluble in alcohol and lipids, and poorly soluble in water. Carmustine is administered by intravenous infusion after reconstitution as recommended Although it is generally agreed that carmustine alkylates DNA and RNA, it is not cross resistant with other alkylators. As with other nitrosoureas, it may also inhibit several key enzymatic processes by carbamoylation of amino acids in proteins.

Carmustine is indicated as palliative therapy as a single agent or in established combination therapy with other approved chemotherapeutic agents in brain tumors such as glioblastoma, brainstem glioma, medullobladyoma, astrocytoma, ependymoma, and metastatic brain tumors. Also it has been used in combination with prednisone to treat multiple myeloma. Carmustine has proved useful, in the treatment of Hodgkin's Disease and in non-Hodgkin's lymphomas, as secondary therapy in combination with other approved drugs in patients who relapse while being treated with primary therapy, or who fail to respond to primary therapy.

Sterile carmustine is commonly available in 100 mg single dose vials of lyophilized material. The recommended dose of carmustine as a single agent in previously untreated patients is 150 to 200 mg/m$^2$ intravenously every 6 weeks. This may be given as a single dose or divided into daily injections such as 75 to 100 mg/m$^2$ on 2 successive days. When carmustine is used in combination with other myelosuppressive drugs or in patients in whom bone marrow reserve is depleted, the doses should be adjusted accordingly. Doses subsequent to the initial dose should be adjusted according to the hematologic response of the patient to the preceding dose. It is of course understood that other doses may be used in the present invention for example 10 mg/m$^2$, 20 mg/m$^2$, 30 mg/m$^2$ 40 mg/m$^2$ 50 mg/m$^2$ 60 mg/m$^2$ 70 mg/m$^2$ 80 mg/m$^2$ 90 mg/m$^2$ 100 mg/m$^2$. The skilled artisan is directed to, "Remington's Pharmaceutical Sciences" 15th Edition, chapter 61. Some variation in dosage will necessarily occur depending on the condition of the subject being treated. The person responsible for administration will, in any event, determine the appropriate dose for the individual subject.

ii. Lomustine

Lomustine is one of the nitrosoureas used in the treatment of certain neoplastic diseases. It is 1-(2-chloro-ethyl)-3-cyclohexyl-1 nitrosourea. It is a yellow powder with the empirical formula of $C_9H_{16}ClN_3O_2$ and a molecular weight of 233.71. Lomustine is soluble in 10% ethanol (0.05 mg per mL) and in absolute alcohol (70 mg per mL). Lomustine is relatively insoluble in water (<0.05 mg per mL). It is relatively unionized at a physiological pH. Inactive ingredients in lomustine capsules are: magnesium stearate and mannitol.

Although it is generally agreed that lomustine alkylates DNA and RNA, it is not ross resistant with other alkylators. As with other nitrosoureas, it may also inhibit several key enzymatic processes by carbamoylation of amino acids in proteins.

Lomustine may be given orally. Following oral administration of radioactive lomustine at doses ranging from 30 mg/m$^2$ to 100 mg/m$^2$, about half of the radioactivity given was excreted in the form of degradation products within 24 hours. The serum half-life of the metabolites ranges from 16 hours to 2 days. Tissue levels are comparable to plasma levels at 15 minutes after intravenous administration.

Lomustine has been shown to be useful as a single agent in addition to other treatment modalities, or in established combination therapy with other approved chemotherapeutic agents in both primary and metastatic brain tumors, in patients who have already received appropriate surgical and/or radiotherapeutic procedures. It has also proved effective in secondary therapy against Hodgkin's Disease in combination with other approved drugs in patients who relapse while being treated with primary therapy, or who fail to respond to primary therapy.

The recommended dose of lomustine in adults and children as a single agent in previously untreated patients is 130 mg/m² as a single oral dose every 6 weeks. In individuals with compromised bone marrow function, the dose should be reduced to 100 mg/m² every 6 weeks. When lomustine is used in combination with other myelosuppressive drugs, the doses should be adjusted accordingly. It is understood that other doses may be used for example, 20 mg/m² 30 mg/m², 40 mg/m², 50 mg/m², 60 mg/m², 70 mg/m², 80 mg/m², 90 mg/m², 100 mg/m², 120 mg/m² or any doses between these figures as determined by the clinician to be necessary for the individual being treated.

g. Miscellaneous Agents

Some chemotherapy agents do not qualify into the previous categories based on their activities. However, it is contemplated that they are included within the method of the present invention for use in combination therapies of cancer with gene therapy involving lipid formulations. They include amsacrine, L-asparaginase, tretinoin, and Tumor Necrosis Factor (TNF), some of which are discussed below.

i. Tumor Necrosis Factor

Tumor Necrosis Factor (TNF; Cachectin) is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-α also has been found to possess anti-cancer activity.

4. Other anti-cancer therapies

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

It is contemplated that other therapies and agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adehesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abililties of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adehesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy also may be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

5. Combination Therapy

Various combinations of any of the above-described anti-hyperproliferative therapies may be employed; for example, gene therapy is "A" and the radio- or chemotherapeutic agent is "B":

A/B/A B/A/B B/B/A A/A/B A/B/B B/A/A A/B/B/B B/A/ B/B

B/B/B/A B/B/A/B A/A/B/B A/B/A/B A/B/B/A B/B/A/A B/A/B/A B/A/A/B A/A/A/B B/A/A/A A/B/A/A A/A/B/A

The terms "contacted" and "exposed," when applied to a cell, are used herein to describe the process by which a therapeutic construct and an anti-hyperproliferative agent are delivered to a target cell or are placed in direct juxtaposition with the target cell. To achieve cell killing or stasis, both agents are delivered to a cell in a combined amount effective to kill the cell or prevent it from dividing.

G. Determining "Bystander Activity"

C-CAM1 is suspected of having a bystander effect, which describes the ability of a first cell that expresses C-CAM1 to exert an effect on a nearby or neighboring second cell because of C-CAM-1 expression and thus activity in the first cell. C-CAM1 may cause soluble factors to be released from the cell expressing C-CAM1, such that cells transfected or transduced cells with C-CAM1 may provide a bystander effect on neighboring hyperproliferative cells. Thus, it is contemplated that the therapeutic C-CAM1 expression construct may be delivered to normal cells and the released bystander effector would produce anti-tumor effects, particularly with respect to adjacent or contiguous hyperproliferative cells. Untransfected cells may experience a therapeutic benefit from C-CAM1 due to the expression of C-CAM1 in transfected cells.

Anti-angiogenic activity can be measured in various ways, and these can be applied to studying and measuring bystander activity. C-CAM1 polypeptides in the present invention have demonstrated anti-angiogenic effects. It is not clear however, whether the C-CAM1 polypeptides are directly or indirectly inhibiting angiogenesis. Thus, in one embodiment of the invention, it is contemplated to more specifically define the role of C-CAM1 on angiogenesis. The following are examples contemplated as useful for determining bystander activity. Usually, time course studies will be performed and each data point should be confirmed by duplicate or triplicate samples. First, one may undertake simple cell counts, usually performed as a function of unit volume or based on the total number of cells in a culture container. Counting can be performed by automated analysis, such as FACS, or manually by microscopic methods. Staining of cells is optional, but may improve the ease and accuracy of some methods.

Preferably, inhibition of cell proliferation is as measured by a decrease in $^3$H-thymidine incorporation. A typical study measures the effects observed in cell conditioned medium obtained 24, 48 and 72 hours after the introduction of a transcriptionally active plasmid or viral vector into the cell.

It is observed in the present invention that C-CAM1 conditioned medium inhibits the in vitro proliferation of endothelial cells. Condition media assays of human umbilical vein endothelial (HUVE) cells demonstrate C-CAM1 conditioned medium inhibits HUVE cell proliferation by 50% as compared to control condition medium. Similar results are observed when the C-CAM1 condition medium is incubated with primary endothelial cells from human pulmonary artery. It is contemplated in the present invention that the inhibitory factor present in the C-CAM1 condition medium can be identified and purified by assaying for specific anti-angiogenic compounds or novel compounds. For example, the concentration of VEGF in the C-CAM1 condition medium was measured in the present invention by ELISA and RNase protection assays, with no significant changes observed compared to control condition medium, suggesting that C-CAM1 does not affect VEGF secretion. It is desirable in the present invention to perform assays similar to those described on a variety of compounds to identify and purify the anti-angiogenic compound or compounds present in the C-CAM1 condition medium.

Thus, in another embodiment, conditioned media or a factor purified therefrom may be used, in accordance with the present invention, to inhibit tumor growth and/or angiogenesis and further to treat cancer.

H. Injectable Compositions and Delivery

The methods of the present invention involve administering therapeutic compositions to a cell or to a subject. The routes of administration will vary, naturally, with the location and nature of the lesion, and include, e.g., intradermal, transdermal, parenteral, intravenous, intramuscular, intranasal, subcutaneous, percutaneous, intratracheal, intraperitoneal, intratumoral, perfusion, lavage, direct injection, and oral administration and formulation. The formulations of the invention may be administered 1, 2, 3, 4, 5, 6, 7, 8, 9, 10, 11, 12, 13, 14, 15, 16, 17, 18, 19, 20, 21, 22, 23, 24, 25, or more times. They may also be administered 1, 2, 3, 4, 5, 6, 7, 8 or more times a day, or they maybe administered every 1, 2, 3, 4, 5, 6, or 7 days, or every 1, 2, 3, 4, or 5 weeks, or every 1, 2, 3, 4, 5, 6, 7, 8, 9, 10, 11, or 12 months.

Intratumoral injection, or injection into the tumor vasculature is specifically contemplated for discrete, solid, accessible tumors. Local, regional or systemic administration also may be appropriate. For tumors of >4 cm, the volume to be administered will be about 4–10 ml (preferably 10 ml), while for tumors of <4 cm, a volume of about 1–3 ml will be used (preferably 3 ml). Multiple injections delivered as single dose comprise about 0.1 to about 0.5 ml volumes. The expression construct or polypeptide may advantageously be contacted by administering multiple injections to the tumor, spaced at approximately 1 cm intervals.

In the case of surgical intervention, the present invention may be used preoperatively, to render an inoperable tumor subject to resection. Alternatively, the present invention may be used at the time of surgery, and/or thereafter, to treat residual or metastatic disease. For example, a resected tumor bed may be injected or perfused with a DOTAP:Cholesterol formulation comprising a nucleic acid construct encoding an anti-proliferative protein. The perfusion may be continued post-resection, for example, by leaving a catheter implanted at the site of the surgery. Periodic post-surgical treatment also is envisioned.

Continuous administration also may be applied where appropriate, for example, where a tumor is excised and the tumor bed is treated to eliminate residual, microscopic disease. Delivery via syringe or catherization is preferred. Such continuous perfusion may take place for a period from about 1–2 hours, to about 2–6 hours, to about 6–12 hours, to about 12–24 hours, to about 1–2 days, to about 1–2 wk or longer following the initiation of treatment. Generally, the dose of the therapeutic composition via continuous perfusion will be equivalent to that given by a single or multiple injections, adjusted over a period of time during which the perfusion occurs.

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

In certain embodiments, the tumor being treated may not, at least initially, be resectable. Treatments with therapeutic liposomal formulations may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two-week period. The two-week regimen may be repeated one, two, three, four, five, six or more times. During a course of treatment, the need to complete the planned dosings may be re-evaluated.

The preferred method of the lipid:nucleic acid expression construct delivery to hyperproliferative cells in the present invention is via intravenous injection. However, the pharmaceutical compositions disclosed herein may alternatively be administered parenterally, intradermally, intramuscularly, or even intraperitoneally as described in U.S. Pat. Nos. 5,543,158; 5,641,515 and 5,399,363 (each specifically incorporated herein by reference in its entirety). Injection of nucleic acid constructs may be delivered by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions or liposomal suspension, particularly multi-vial formulations, of the active compounds as free base or pharmacologically acceptable salts may be prepared in water, in buffered solutions, and suitably mixed with a surfactant, such as hydroxypropylcellulose. Dispersions may also be prepared in glycerol, liquid polyethylene glycols, and mixtures thereof and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin. For multi-viral formulations the carrier compounds, the liposome, prepared in sterile suspensions that are suitable for deliver to humans.

For single viral formulations, suspensions of the active compounds in the liposome carrier with and without additional components may be used as descibed in the instant application.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage maybe dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds and carriers in the required amount in the appropriate solvent with various of the other ingredients enumerated above, as required, prepared by aseptic procedure and/or followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of associated protein(s)) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

I. Additional Modes of Delivery

In addition to the methods of delivery described above, the following techniques are also contemplated as alternative methods of therapeutic nucleic acid delivery. Sonophoresis (i.e., ultrasound) has been used and described in U.S. Pat. No. 5,656,016 (specifically incorporated herein by reference in its entirety) as a device for enhancing the rate and efficacy of drug permeation into and through the circulatory system. Similarly, electroporation has been used to deliver genes in vivo (Suzuki et al., 1998). Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. No. 5,770,219 and U.S. Pat. No. 5,783,208), rectal delivery (U.S. Pat. No. 5,811,128) and feedback controlled delivery (U.S. Pat. No. 5,697,899), each specifically incorporated herein by reference in its entirety.

J. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cells. The DU145 prostate cancer cells were purchased from ATCC. Normal human primary endothelial cells originally derived from human umbilical vein endothelial cells (HUVEC) and human pulmonary artery endothelial cells (HPAEC), respectively, were purchased from CLONETICS Corp. (San Diego, Calif.) and cultured according to manufacture's procedures. Normal human primary epithelial cells originally derived from human kidney proximal tubule were purchased from CLONETICS Corp. (San Diego) and maintained in the medium as specified. In some cases, normal human umbilical endothelial cells were isolated and maintained in EGM-2 medium (CLONETICS).

Preparation of C-CAM1 Condition Medium. DU145 cells at 80% confluence were infected with Ad-CAM1, Ad-β-gal, or Ad-AS-CAM1 at an MOI of 10 for 48 hr. The media were collected and the pH of the medium were adjusted to 7.4 with sodium bicarbonate.

In Vitro Endothelial Cell Proliferation Assays. Confluent endothelial cell cultures were dispersed and plated at a density of $10^5$ cells per well (in 6-well plates) in EGM-2 medium. After overnight incubation, conditioned medium from DU145 cells ($1 \times 10^6$ cells/100-mm dish) infected with either Ad-AS-C-CAM1 (as a control) or Ad-C-CAM1 were added. After 48 h of treatment, total cell numbers were counted under direct microscope examination.

Assay for Apoptosis. Using flow cytometry, apoptosis was analyzed by DNA content in nuclei isolated by detergent-mediated cytolysis. FACScan flow cytometer was used (Becton Dickinson, San Jose, Calif.) equipped with an argon-ion laser (15 milliwatt, 488 nm). Fragmented nuclei are detected as particles with fractional DNA content merging before the G0/G1 peaks (sub-G1-cells).

Co-culture of DU145 and HUVE cells. Confluent HUVE cell cultures were dispersed and plated at a density of 105 cells per well (in 6-well plates) in EGM-2 medium. These endothelial cells were allowed to attach to the plate for 4 hours before the culture inserts containing semipermeable membrane were placed into the well and DU145 cells were plated into the inserts at a density of 0.3 million cells per well. DU145 cells were infected with Ad-AS-C-CAM1 (as a control), Ad-C-CAM1, Ad-CAM1-cyto, Ad-myr-CAM1-cyto, Ad-CAM1-cyto-S503A, or Ad-CD66a at an MOI of 10. After 48 h of incubation, both DU145 cells and endothelial cells were collected by trypsin digestion and apoptosis was determined by DNA content analysis.

Example 2

C-CAM1 Condition Medium Inhibits the in vitro Proliferation of the Endothelial Cell To investigate whether suppression of in vivo tumor growth by C-CAM1 was due to an anti-angiogenic effect or direct anti-tumor activity, the conditioned media were collected from DU145 cells infected with Ad-C-CAM1 or control virus. These conditioned media were tested for their ability to inhibit proliferation of DU145 prostate tumor cells or human umbilical vein endothelial (HUVE) cells in vitro.

Neither condition medium had any effect on DU145 cell proliferation in vitro, as assessed by cell numbers. However, when these condition media were assayed with HUVE cells, C-CAM1 condition medium inhibited HUVE cell proliferation by 50% as compared to the control condition medium. Since direct addition of Ad-C-CAM1 or control virus to HUVE cells did not have effect on their proliferation, the factor that inhibited HUVE cell growth must be in the C-CAM1 condition medium.

That C-CAM1 condition medium inhibits HUVE cells but not DU145 cells might be due to the fact that HUVE cells are primary cells from normal tissues, whereas DU145 cells are from tumor. To rule out this possibility, the inventors tested another primary epithelial cell culture from human kidney proximal tubule and found that neither condition medium has any effect on the growth of kidney proximal tubule epithelial cells. This observation suggests that inhibition of HUVE cell growth by C-CAM1 condition medium is likely specific to the endothelial cell type.

Further tests were performed to determine whether the inhibitory factor in C-CAM1 condition medium can also inhibit other types of endothelial cells. The same condition media were incubated with primary endothelial cells from human pulmonary artery. Significant inhibition of these artery endothelial cells was also observed with C-CAM1 condition medium but not the control condition medium, suggesting that the inhibitory factor in C-CAM1 condition medium is also effective towards artery endothelial cells.

Example 3

Induction of Endothelial Cell Apoptosis

Figure 1B:
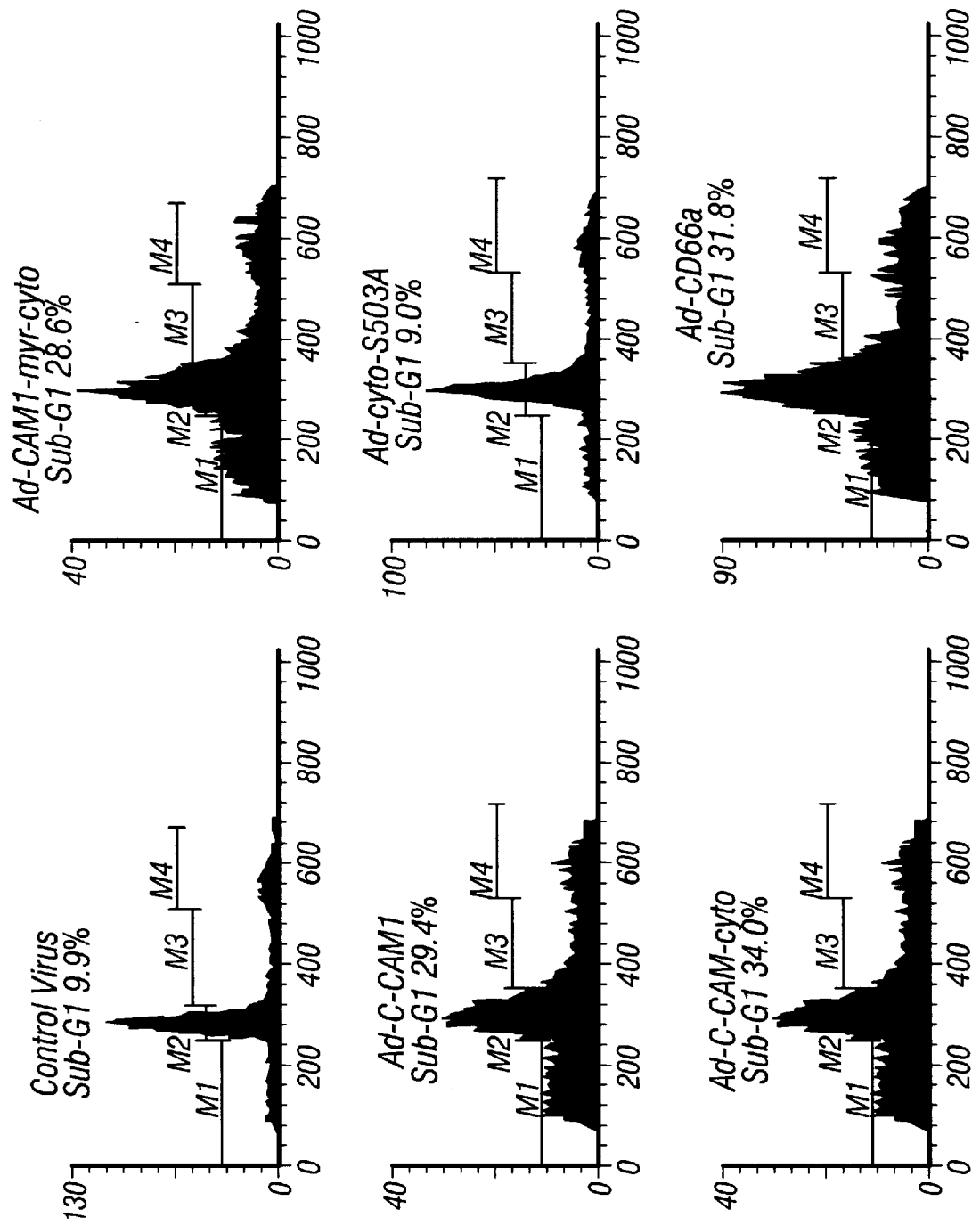
FIG. 1B. Induction of endothelial cell apoptosis by C-CAM1 mutants correlated with their tumor suppressive activities.

The inventors examined whether C-CAM1 condition medium-induced endothelial cell growth inhibition resulted from increased programmed cell death. Propidium iodide staining of DNA followed with fluorescence activated cell sorting showed the presence of significant sub-G1 population in C-CAM1 condition medium-treated HUVE cells as compared to those treated with control condition medium (FIG. 1). Similar results were obtained with human pulmonary artery endothelial cells treated with C-CAM1 conditioned medium (FIG. 1). These results suggest that decreased growth of endothelial cells that had been treated with C-CAM1 condition medium resulted from increased apoptosis. Table 5 demonstrates the effect of C-CAM mutants on cell cycle distribution.

TABLE 5

Effect of C-CAM1 mutants on the cell cycle distribution of HUVE and DU145 cells in a co-culture system.

|  | AS-CAM1 | C-CAM1 | CAM-cyto | myr-CAM-cyto | cyto-S503A | CD66a |
|---|---|---|---|---|---|---|
| Human Umbilical Endothelial Cells | | | | | | |
| Sub-$G_1$ | 9.9 | 29.4 | 34.0 | 28.6 | 9.0 | 31.8 |
| $G_1/G_0$ | 71.1 | 46.1 | 36.0 | 41.2 | 72.5 | 38.0 |
| S | 8.6 | 15.0 | 19.4 | 21.6 | 8.7 | 21.8 |
| $G_2/M$ | 11.8 | 9.6 | 11.3 | 11.1 | 10.3 | 9.2 |
| DU145 Cells | | | | | | |
| Sub-$G_1$ | 20.5 | 27.0 | 20.2 | 19.8 | 16.8 | 22.0 |
| $G_1/G_0$ | 44.6 | 41.5 | 44.0 | 35.1 | 44.6 | 44.2 |
| S | 20.1 | 17.8 | 18.2 | 24.4 | 21.0 | 15.2 |
| $G_2/M$ | 16.4 | 15.2 | 18.5 | 19.5 | 17.9 | 20.5 |

Example 4

Induction of Endothelial Cell Apoptosis by C-CAM1 Mutants Correlated with their Tumor Suppressive Activities The effects of various C-CAM1 mutants on endothelial cells growth were examined in a co-culture system. After 48 hr of incubation, both DU145 and HUVE cells ere collected and their DNA contents determined by propidium iodide staining. A significant sub-G1 population, which is indicative of apoptosis, was detected in HUVE cells incubated with Ad-CAM1, Ad-CAM1-cyto, Ad-myr-CAM1-cyto, and Ad-CD66a (human homologue of C-CAM1). In contrast, control virus and Ad-CAM1-cyto-S503A (a C-CAM1 mutant without tumor suppressor function) treated HUVE cells did not have significant apoptosis. Thus, induction of endothelial cell apoptosis by C-CAM1 mutants correlated with their tumor suppression effects. This in turn suggests that C-CAM1-mediated tumor suppression in vivo is partly due to its ability to induce the release of an C-CAM1 or C-CAM1 cytoplasmic domain.

Example 5

Preliminary Characterization of the Angiogenesis Inhibitor

The concentration of VEGF in the condition medium was measured by ELISA and there is no significant difference between DU145 cells treated with Ad-C-CAM1 and control virus. This observation suggests that expression of C-CAM1 does not affect VEGF secretion. In addition, RNase protection using a set of angiogenesis related genes was performed on RNA samples isolated from DU145 cells treated with Ad-C-CAM1 or control virus. RNase protection showed that not only VEGF message remained unchanged, consistent with the ELISA measurement, Ad-C-CAM1 also did not have any effect on the steady-state message levels of VEGF-C, angiopoietin, Tie-1, and thrombin receptor. Thus, C-CAM1's anti-angiogenesis effect is not mediated by inhibition of these known angiogenic factors, suggesting that it might involve a novel factor.

Example 6

Materials and Methods

Construction of expression vectors and generation of recombinant adenovirus. C-CAM1 mutants containing only the cytoplasmic domain (CAM1-cyto and CAM1-myr-cyto) were constructed as follows. A translation initiation codon (ATG) was inserted at the N terminus of the cytoplasmic domain by PCR. An oligonucleotide (oligo 53, SEQ ID NO. 4 AAGCTTATGTCCAGGAAGACTGGCGGGGGA), that contains a HindIII restriction site, a methionine codon, and nucleotides 1345–1365 of C-CAM1 (Lin and Guidotti, 1989) was synthesized and used as the 5' primer. Another oligonucleotide, oligo 54, which contained a sequence complementary to nucleotides 1540–1560 of C-CAM1 and a NotI restriction site, was used as the 3' primer. Using oligos 53 and 54 as the primers and the full-length C-CAM1 cDNA (Lin and Guidotti, 1989) as the template in PCR, a 233-bp product that encoded a protein with a methionine appended to the N terminus of the C-CAM1 cytoplasmic domain was obtained. This 233-bp PCR product was subcloned into the plasmid pCRII to produce pCR-CAM1-cyto, and the nucleotide sequence of the double stranded DNA was determined to confirm that no nucleotide substitution had occurred. The 233-bp fragment was digested with HindIII and NotI and inserted into the adenoviral shuttle vector pXCMV at the HindIII/NotI sites to generate pXCMV-CAM1-cyto. To express the C-CAM1 cytoplasmic domain as a membrane-anchored protein, inventors took advantage of the fact that proteins with methionine-glycine at their N termini are often myristylated and become associated with the plasma membrane. pXCMV-CAM1-myr-cyto, an adenoviral shuttle vector containing sequence coding for CAM1-myr-cyto, was generated similarly except that oligo 55 (SEQ ID NO. 5 AAGCTTATGGGATCCAGGAAGACTGGCGGGGGA), which contains a HindIII restriction site, a sequence encoding methionine and glycine, and nucleotides 1345–1365 of C-CAM1 (Lin and Guidotti, 1989), was synthesized and used as the 5' primer. Recombinant adenoviruses containing cDNAs coding for mutant C-CAM1 sequences (Ad CAM1-cyto and Ad CAM1-myr-cyto) were generated in 293 embryonic kidney cells by co-transfection of plasmid pJM17, which contained the adenovirus genome with the E1 region deleted, and C-CAM1 mutants in adenoviral shuttle vectors according to published procedures (Zhang et al., 1993). Generation of recombinant adenoviruses containing wild-type C-CAM1 (Ad C-CAM1) and AS-C-CAM1 (C-CAM1 in antisense orientation, Ad AS C-CAM1) cDNA was described in Kleinerman et al., (1995b). Ad AS C-CAM1, which did not code for protein, was used for viral toxicity control. Generation of mutant C-CAM1 recombinant adenoviruses with cytoplasmic domain deletions, i.e., Ad CAM1-H458, Ad CAM1-G454, and with adhesion domain deletion, i.e., At CAM1-AD1, was described previously (Luo et al., 1997).

Identification of inserts in recombinant adenovirus by PCR. The presence of the desired DNA inserts in the recombinant adenoviruses was confirmed by PCR with primers and recombinant adenoviral DNA samples prepared according to published procedures (Zhang et al., 1993). Specifically, primers XCMVI (SEQ ID NO. 6 GGCCCACCCCCTTGGCTTC) and XCMV2 (SEQ ID NO. 7 TTGTAACCATTATAAGCTGC), which flank the cDNA inserts, were used to confirm the presence and the correct lengths of the desired cDNA inserts, whereas primers XCMV3 (SEQ ID NO. 8 TCGTTTCTCAGCAGCTGTTG) and XCMV4 (SEQ ID NO. 9 CATCTGAACTCAAAGCGTGG) were used to detect the viral genome. All PCRs were performed by published procedures (Zhang et al., 1993).

Immunoblot analysis of C-CAM1 mutant proteins expressed in DU145 cells. DU145 cells were infected with recombinant adenovirus at a multiplicity of infection (MOI) of 10 for 48 h. The cells were then trypsinized. Aliquots of the cell lysate were boiled in SDS sample buffer and analyzed by SDS-polyacrylamide gel electrophoresis (Laemmli, 1970). After electrophoresis, the proteins were transferred to nitrocellulose membranes, exposed to primary rabbit anti-C-CAM antibody Ab669 (Lin et al., 1991) or rabbit anti-cytoplasmic domain antibody anti-C3 (Lin et al., 1991) and secondary antibody (horseradish peroxidase-conjugated goat anti-rabbit IgG), and detected by an enhanced chemiluminescence assay.

Adhesion assays. DU145 cells were infected at an MOI of 10 for 48 h with either the control virus (Ad β-gal, which contains cDNA coding for β-galactosidase) or recombinant adenoviruses that contain C-CAM1 or C-CAM1 mutant cDNA. The infected cells were harvested by trypsin treatment and resuspended in minimal essential medium. Single-cell suspensions of these cells were made by repeated pipetting. The ability of these cells to aggregate was monitored under constant mixing at room temperature. At various time intervals, aliquots of the control cells or the virus-infected cells were removed, and the single cells in these aliquots were counted with a hemocytometer. The relative degree of aggregation was determined by comparing the changes in the numbers of single cells as a function of time.

Measurement of in vivo tumor growth from recombinant adenovirus-infected DU145 cells. DU145 cells were infected with recombinant adenovirus at an MOI of 10 for 48 h. The cells were harvested by trypsin treatment and resuspended in minimal essential medium. Cells ($2 \times 10^6$ in a total volume of 100 ul per site) were injected subcutaneously into the flanks of nu/nu mice. The sizes of the tumors that developed from these DU145 cells were determined weekly by using calipers to measure the length, width and height of the tumor nodules. Tumor sizes were calculated according to the formula of Rockwell et al. (1972).

Example 7

Characterization of C-CAM1 Mutants

Figure 2:
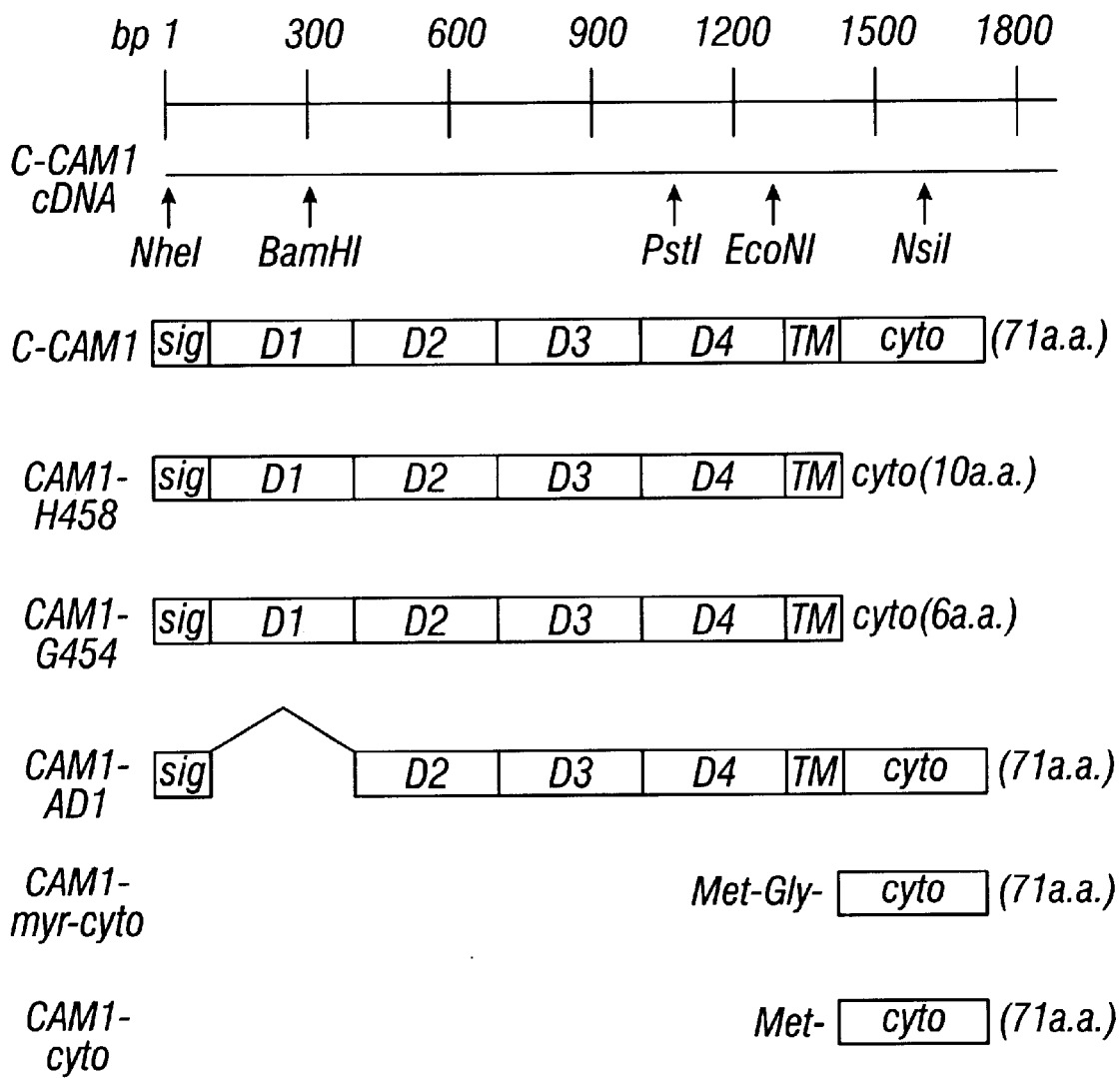
FIG. 2. Mutant C-CAM molecules. Ig-like domains are labeled D1 to D4. sig, signal sequence; TM, transmembrane domain; cyto, cytoplasmic domain; Met, methionine; Gly, glycine.
Figure 3A:
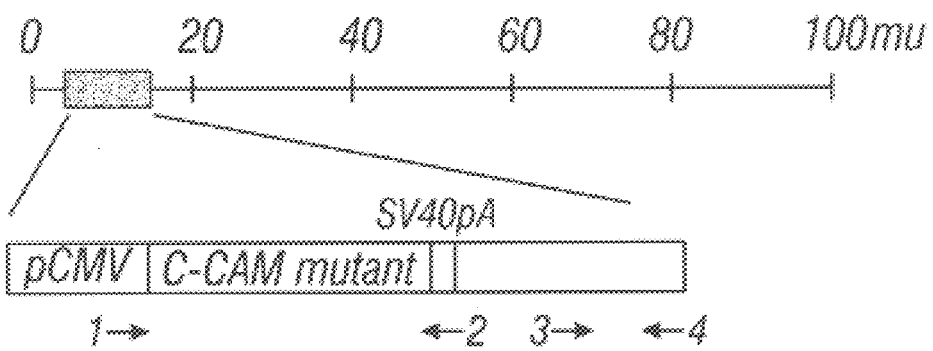
FIG. 3A and FIG. 3B. Analysis of recombinant adenoviruses.
Figure 3B:
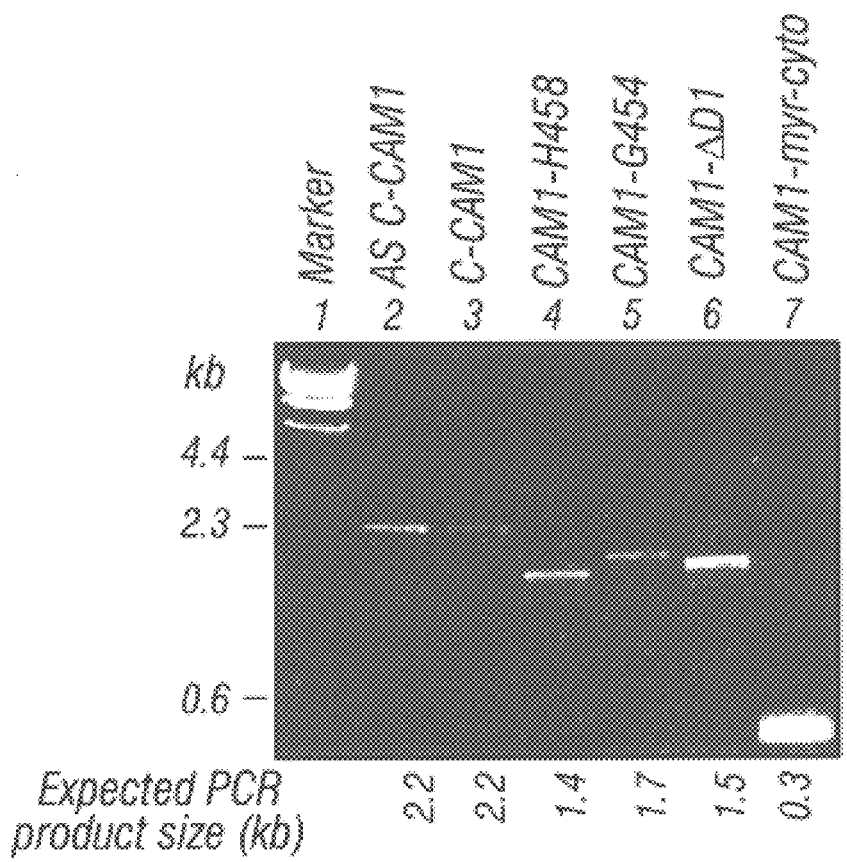

C-CAM1 mutants with the deletions shown in FIG. 2 were constructed and then recombinant adenoviruses containing these mutant cDNAs were generated by homologous recombination. To confirm that no DNA rearrangement or deletion had occurred during recombination, the lengths of these cDNA inserts in the recombinant adenoviruses were examined by a series of polymerase chain reactions (PCRs) using a pair of primers (XCMV1 and XCMV2) that flank the cDNA inserts (FIG. 3A). As shown in FIG. 3B, the sizes of all PCR products matched the predicted sizes of the corresponding DNA fragments, indicating that these recombinant adenoviruses contained the desired mutant C-CAM constructs.

Mutant C-CAM1 proteins expressed in DU145 cells were detected by western immunoblottings with either a polyclonal antibody (Ab669) specific for C-CAM1 or an anti-peptide antibody (anti-C3) specific for its cytoplasmic domain (Lin et al., 1991). Mature C-CAM1 is predicted to be 53 kDa without the signal peptide and glycosylation. When expressed in DU145 cells, the wild-type C-CAM1 protein had an apparent molecular mass of about 120–130 kDa, as revealed by sodium dodecyl sulfate (SDS)-polyacrylamide gel analysis (FIG. 4A). This observation suggested that C-CAM1 protein, which contains 16 potential N-linked glycosylation sites, is heavily glycosylated in DU145 cells, as it is in other cells (Lin and Guidotti, 1989). Similarly, all C-CAM1 mutants containing extracellular domains were also glycosylated. The protein products of mutants lacking the cytoplasmic domain (CAM1-H458 and CAM1-G454) or the adhesion domain (CAM1-AD1) were smaller than normal, as expected. Because of their small sizes, the protein products of mutants containing the cytoplasmic domain alone (CAM1-cyto and CAM1-myr-cyto) were analyzed on a 15% SDS-polyacrylamide gel for western blot analysis. As shown in FIG. 4B, immunoreactive proteins with molecular mass of about 7–8 kDa were detected in cells infected with Ad CAM1-cyto or Ad CAM1-myr-cyto. Thus, the results of the western blot analyses confirmed the successful production of all C-CAM1 deletion mutants in DU145 cells (FIG. 4A and FIG. 4B).

Figure 5:
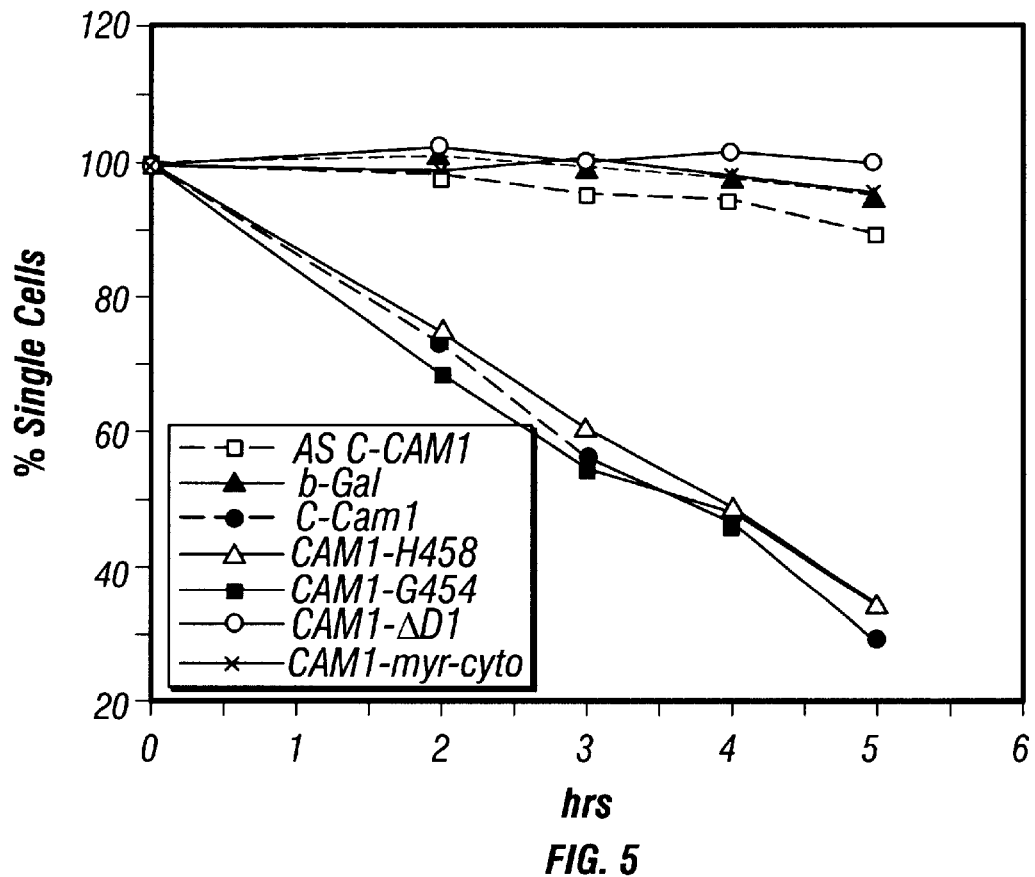
FIG. 5. Creation of DU145 cells expressing C-CAM1 or C-CAM1 mutants. DU145 cells were infected with Ad C-CAM1 and the mutants and controls indicated. The cell adhesion assay was performed as described in Materials and Methods. The aggregation of cells is expressed as decrease in the percentage of single cells.

To determine whether the expressed C-CAM1 mutant proteins were properly folded in DU145 cells, a cell-adhesion function assay was used. Increases in cell aggregation were detected in cells expressing the wild-type C-CAM1, CAM1-H458, and CAM1-G454 but not in cells transfected with CAM1-AD1, CAM1-myr-cyto, or control vectors (AS C-CAM1 and β-gal) (FIG. 5). This result is consistent with previous findings that only the C-CAM1 mutants containing the first Ig domain have adhesion activity (Cheung et al, 1993a). This result also suggests that these mutant C-CAM molecules were properly folded and functional.

Example 8

Effect of C-CAM1 Mutants on the Tumorigenicity of DU145 Cells in vivo

The effects of C-CAM1 and its mutant proteins on the tumorigenicity of DU145 cells in vivo were examined in a nude mouse xenograft model. DU145 cells, which were derived from a human prostate cancer that had metastasized to brain, are tumorigenicity when injected into nude mice (Stone et al., 1978). DU145 cells do not express C-CAM1 message, as assessed by the RNase protection assay with a probe for the cytoplasmic domain of C-CAM1 cDNA (Luo et al., in press). When compared with control parental cells, DU145 cells expressing wild-type C-CAM1 exhibited reduced tumorigenicity, as evidenced by the reduction in tumor incidence and size (Table 6). In comparison, cells infected with control viruses that contained the C-CAM1 sequence in the antisense orientation (Ad AS C-CAM1) did not show reduction in tumor incidence or size, suggesting that the reduced tumorigenicity of C-CAM1 infected cells was caused by C-CAM1 expression (Table 6). Likewise, the mutant lacking the D1 domain (CAM1-AD1) also suppressed the tumorigenicity of DU145 cells, although to a lesser extent (Table 7). In contrast, mutants CAM1-H458 and CAM1-G454, which had shortened cytoplasmic domains, were unable to suppress tumor growth in vivo (Table 7). These results suggested that C-CAM1-mediated tumor suppressive activity did not require the adhesion domain but does require the cytoplasmic domain.

TABLE 6

Effect of wild-type C-CAM1 on tumorigenicity of DU145 cells

| Adenovirus infection | Tumor incidence (%)[a] 30 days | Tumor volume (mm$^3$) ± S.E. 30 days |
|---|---|---|
| Control (no infection) | 30/36 (83%) | 43.7 ± 7.2 |
| Ad AS C-CAMI | 29/36 (81%) | 55.9 ± 10.6 |
| Ad C-CAMI | 0/36 (0%) | 0 ± 0 |

[a]Number of tumors/total number of injection sites. Only tumors larger than 10 mm$^3$ were counted.

TABLE 7

Effect of C-CAM1 mutants on tumorigenicity of DU145 cells

| Adenovirus infection | Tumor incidence (%)[a] | | Tumor volume (mm³) ± S.E. | |
|---|---|---|---|---|
| | 20 days | 30 days | 20 days | 30 days |
| Control (no infection) | 12/18 (67%) | 17/18 (94%) | 11 ± 2 | 40 ± 7 |
| Ad AD C-CAM1 | 14/18 (78%) | 18/18 (100%) | 12 ± 2 | 45 ± 12 |
| Ad C-CAM1 | 0/18 (0%) | 0/18 (0%) | 0 ± 0 | 0 ± 0 |
| Ad CAM1-AD1 | 1/18 (6%) | 5/18 *(28%) | 2 ± 2 | 23 ± 11 |
| Ad CAM1-H458 | 14/18 (78%) | 16/18 (89%) | 17 ± 3 | 65 ± 21 |
| Ad CAM1-G454 | 16/18 (89%) | 18/18 (100%) | 17 ± 2 | 61 ± 13 |

[a]Number of tumors/total number of injection sites. Only tumors larger than 10 mm³ were counted.

Although the cytoplasmic domain of C-CAM1 was required for its tumor-suppressive activity, it was not clear whether the transmembrane domain and Ig domains also contributed to the tumor-suppressive activity. To answer this question, it was investigated whether the cytoplasmic domain by itself was sufficient to suppress the tumorigenicity of DU145 cells in vivo. To preserve the membrane proximity of the cytoplasmic domain, a potential myristylation sequence in the cytoplasmic clone was included. As shown in Table 8, expression of this clone (CAM1-myr-cyto) suppressed the tumorigenicity of DU145 cells. In addition, also tested was a clone without the myristylation sequence (CAM1-cyto). As shown in Table 8, there was no significant difference between these two clones, suggesting that the myristylation sequence is not required. In any event, this result indicated that C-CAM1's tumor-suppressive activity did not require its extracellular or transmembrane domains and that the cytoplasmic domain of C-CAM1 was necessary and sufficient for suppressing the tumorigenicity of prostate cancer cells.

TABLE 8

Effect of C-CAM1 cytoplasmic domain on tumorigenicity of DU145 cells

| Adenovirus infection | Tumor incidence (%)[a] | | Tumor volume (mm³) ± S.E. | |
|---|---|---|---|---|
| | 30 days | 51 days | 30 days | 51 days |
| Ad AS C-CAM1 | 12/12 (100%) | 12/12 (100%) | 28 ± 4 | 163 ± 56 |
| Ad CAM1-myr-cyto | 0/12 (0%) | 0/12 (0%) | 0 ± 0 | 0 ± 0 |
| Ad CAM1-cyto | 0/12 (0%) | 0/12 (0%) | 0 ± 0 | 0 ± 0 |

[a]Number of tumor/total number of injection sites. Only tumors larger than 10 mm³ were counted.

Example 9

Materials and Methods

Cells. The DU145 prostate cancer cells were purchased from ATCC. Normal human primary endothelial cells were derived from 3 tissue sources. Human umbilical vein endothelial cells (HUVEC), and human pulmonary artery endothelial cells (HPAEC), and human neonatal dermal microvascular endothelial cells (HMNVEC-nd), were all purchased from CLONETICS Corp (San Diego, Calif.) and cultured according to manufacturer's procedure, in media supplied by manufacturer. Normal human primary epithelial cells derived from human kidney proximal tubules were purchased from CLONETICS Corp (San Diego) and maintained in the medium specified.

Preparation of C-CAM1 Conditioned Media (CM). Generation of wild type and mutant C-CAM1 recombinant adenoviruses was carried out as previously described (Luo et al., 1997; Luo et al., 1999). Briefly, conditioned media (CM) was collected after incubating DU145 cells ($1\times10^6$ cells in 10 ml DMEM-F12 with 5% FBS) with Ad-C-CAM1 or Ad-Luc at an MOI of 10 for 48 hr. The media were removed and the pH of each medium adjusted to 7.4 with sodium bicarbonate. Media used for in vivo and in vitro angiogenesis assays were concentrated 50 fold with an AMICON dialysis unit with 10 kDa molecular weight cut off (AMICON Corporation, Lexingon, Mass.).

Endothelial Cell Migration Assay. In vitro endothelial cell migrations were performed as previously described (Polverini et al., 1985) in a modified Boyden chamber where cells migrated from the lower to the upper well through gelatinized 8 mm Nucleopore membrane (Nucleopore Corp.). Briefly, the cells were loaded in inverted chambers at $2.5\times10^5$ cells per well, incubated for 2 hr to allow attachment, the chambers were then re-inverted and test materials added to the top well. The cells were allowed 3–4 hrs to migrate, the chambers then disassembled, membranes fixed and stained. DME supplemented with 0.1% BSA was used as a negative control and VEGF at 100 pg/ml as a positive control. Conditioned media were tested at 10 and 20 mg/ml. Each sample was tested in quadruplicate for statistical evaluation. The data are reported as cell migrated per 10 high powered fields.

RNase Protection Assay. DU145 cells were infected with recombinant adenovirus at an MOI of 10 for 48 hr. Total RNA was extracted from cells by the single-step acid guanidinium-phenol-chloroform extraction method (Chomcyzynski et al., 1987). Ten µg of RNA samples were used for RNase protection assay with a set of angiogenesis related genes (multi-probe template set, hANGIO-1 (PHARMINGEN)) according to procedures provided by the manufacturer.

Determination of VEGF Concentration. Conditioned medium (CM) from DU145 cells, DU145 cells infected with control, or Ad-C-CAM1 for 48 h was collected. Concentration of VEGF in the conditioned medium was measured by using ELISA with the human VEGF QUANTIKINE Kit (R & D Systems, Minneapolis Minn.).

Corneal Neovascularization Assay. For in vivo angiogenesis assay, slow release HYDRON pellets (HYDRON Laboratories, New Brunswick, N.J.) of approximately 5 µl were formulated and implanted aseptically into the cornea of female Fisher 344 rats (120–140 g) as previously described (Polverini et al., 1985). All compounds in the pellets were used at concentrations at least 10 fold higher than those used in the migration assay in order to account for the diffusion from a slow release pellet. Neovascularization was assessed on day 7, post implantation by slit-lamp microscopy. Directional growth of capillary blood vessels from the peripheral limbal plexus into avascular corneal stroma was considered a positive response.

In Vitro Endothelial Cell Proliferation Assays. On day 0 confluent HUVECs were harvested, dispersed in 2 ml EBM-2 medium (Clonetics, San Diego, Calif.) and plated in 6-well plates at a density of $2\times10^5$ cells per well. On day 1, conditioned medium from control DU145 cells infected with either Ad-Luc or DU145 infected with Ad-C-CAM1 was added to the cultures. After 48 hr treatment the cells were harvested by trypsinization and total cell numbers determined by direct microscopic examination.

Apoptosis Assay. Apoptosis was demonstrated by 2 methods: (1) the analysis of DNA content in the nuclei isolated by detergent-mediated cytolysis followed with FACS analysis according to Vindelov (1983) using FACScan flow cytometer (Becton Dickinson, San Jose, Calif.) equipped with an argon-ion laser (15 milliwatt, 488 nm). The red fluorescence, generated by propidium iodide, was captured by the FL3 channel. Fragmented nuclei can be seen as particles with fractionated DNA content located on the DNA histograms to the left of the G0/G1 peak (sub-G1-cells); (2) DNA ladder analysis was performed by digesting the nuclei fraction with proteinase K and the DNA was separated on an agarose gel.

Co-Culture of DU145 and HUVECs. The effects of various C-CAM1 mutants on HUVECs were performed in a co-culture system. Briefly, HUVECs ($2 \times 10^5$ cells/well) in EBM-2 medium were plated onto a 6-well plate overnight. DU145 cells were loaded in inner chambers at $2 \times 10^5$ cells per well, incubated overnight to allow attachment. The chambers were then transferred to the plate containing HUVECs and test materials, i.e., Ad-Luc, Ad-C-CAM1, Ad-CAM1-cyto, Ad-CAM1-gly-cyto, Ad-CAM1-S503A, or Ad-CD66a were added to the top well at a viral to cell ratio of 10. After 48 hr treatment, the cells were harvested by trypsinization and prepared for apoptosis assay as described above.

Example 10

Figure 6:
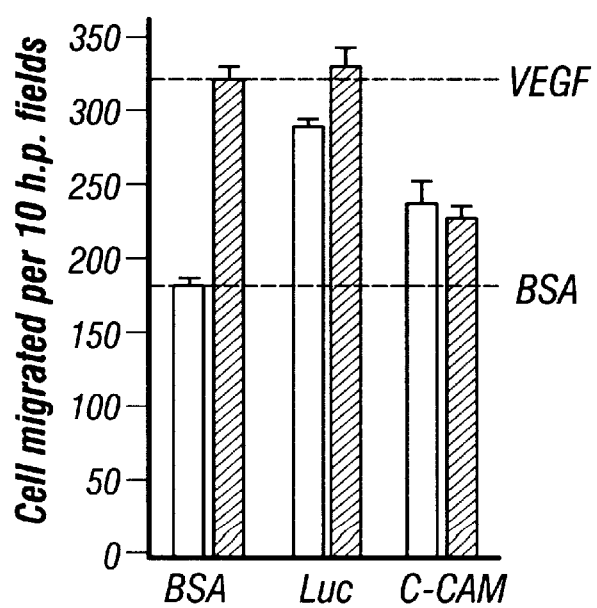
FIG. 6. Effects of CM on migration of cultured capillary endothelial cells. CM harvested from control (Luc) and C-CAM1 expressing cells was collected and tested for its ability to inhibit migration of capillary endothelial cells in the presence and absence of VEGF.

Media Conditioned by Ad-C-CAM1-Infected Cells Inhibited Endothelial Cell Migration To study the potential anti-angiogenic effect from C-CAM1, conditioned media (CM) were collected from DU145 cells infected with Ad-C-CAM1 or control virus (Ad-Luc) and tested for their ability to affect endothelial cell migration in vitro. Medium conditioned by control virus-infected cells (Luc) induced endothelial cell migration at levels similar to those induced by VEGF (100 pg/ml) alone. In contrast, C-CAM1 CM effectively blocked endothelial cell migration up the gradient of stimulatory VEGF (FIG. 6). Media conditioned by DU145 cells contained 650 pg/ml/100,000 cells of VEGF as measured by ELISA, suggesting that DU145 cells can secrete VEGF. Interestingly, Ad-C-CAM1 infection had no significant effect on the levels of secreted VEGF. Neither did Ad-C-CAM1 infection influence the expression of other pro-angiogenic molecules, such as angiopoietin, Tie, and endoglin, in DU145 cells by RNase protection assay using multi-probe template set, hANGIO-1 (PHARMINGEN). Taken together these observations suggest that C-CAM1 up-regulates inhibitory factor or factors (IF) that were anti-angiogenic, rather than down-regulates angiogenic stimuli, such as VEGF.

Example 11

C-CAM1 Conditioned Medium Inhibits Neovascularization in vivo

The ability of C-CAM1 conditioned medium to inhibit neovascularization in vivo was tested in a rat corneal neovascularization assay. Non-inflammatory slow release pellets containing C-CAM1 or control conditioned medium, alone or in combination with bFGF were surgically implanted in avascular rat cornea and examined on day 7 post implantation for directional capillary ingrowth. Control CM from Luc infected cells (Luc CM) induced vigorous capillary ingrowth into the cornea, that was likely due to the presence of stimulatory VEGF. However, C-CAM1 CM completely lacked this neovascularization activity and completely inhibited bFGF-induced neovascularization (Table 9). These observations point to the fact that anti-angiogenic factor or factors in C-CAM1 CM blocked both bFGF- and VEGF- induced neovascularization, and are possibly active against wider variety of angiogenic stimuli.

TABLE 9

C-CAM1 conditioned medium inhibits corneal neovascularization.

| Sample No. | Sample composition | Responses + | +/− | − | Comments |
|---|---|---|---|---|---|
| 1 | bFGF, 100 ng/ml | 3 | 0 | 0 | 3/3 |
| 2 | Luc, 200 ug/ml | 2 | 1 | 0 | 3/3 |
| 3 | bFGF, 100 ng/ml + Luc | 3 | 0 | 0 | 3/3 |
| 4 | C-CAM, 200 ug/ml | 0 | 0 | 3 | 0/3 |
| 5 | bFGF, 100 ng/ml + C-CAM | 1 | 0 | 2 | 1/3 |

Example 12

C-CAM1 -Conditioned Medium Inhibits Endothelial Cell Proliferation

To investigate the mechanisms underlying anti-angiogenic activity induced by C-CAM1, in vitro effect of C-CAM1 CM on proliferation of endothelial cells was tested. Neither control nor C-CAM1-conditioned medium had any effect on proliferation of DU145 cells in culture. However, proliferation of the large vessel endothelial cells (HUVECs) was decreased by 50% in the presence of C-CAM1 CM as compared to control Luc CM. Direct addition of Ad-C-CAM1 or control virus (Ad-Luc) had no effect on the proliferation of HUVECs suggesting that the inhibition of endothelial cell growth is not due to the immediate presence of C-CAM1 but rather to a C-CAM1-induced secretion of a secondary factor into conditioned medium.

It is possible that C-CAM1 conditioned medium exhibited inhibitory effect on HUVECs but not DU145 cells because HUVE cells is primary cells while DU145 cells is an established tumor cell line. To examine this possibility, the effect of C-CAM1 CM on a primary epithelial cell culture derived from human kidney proximal tubule was tested. Neither control CM nor C-CAM 1 CM had an effect on the growth of these epithelial cells.

To further test whether the inhibitory compounds in C-CAM1 conditioned medium affect other endothelial cell subtypes, the same CM were also used to treat primary endothelial cells generated from human pulmonary artery (HPAEC). Significant growth inhibition of HPAECs by C-CAM1 CM was observed when compared to control-conditioned medium, suggesting that the inhibitory factor(s) in C-CAM1 conditioned medium has no specificity for one particular type of endothelial cells.

Example 13

Induction of Endothelial Cell Apoptosis

Several inhibitors of angiogenesis are capable of inducing endothelial cell apoptosis (Dhanabal et al., 1999; Jimenez et al., 2000). C-CAM1 CM was also analyzed for the ability to initiate programmed cell death in endothelial cells. Propidium iodide (PI) staining of DNA followed by FACS analysis showed the presence of significant sub-G1 population, indicative of apoptotic cells, among HPAECs treated with C-CAM1 CM compared to those incubated with control CM. Similar results were obtained with HUVECs treated with C-CAM1 conditioned medium. In addition, increased DNA fragmentation was also observed in HUVEC treated with C-CAM1-conditioned medium. These results suggest that the decrease in proliferation of HPAECs and HUVECs upon incubation with C-CAM1 conditioned medium is most likely due to an increase in programmed cell death rather than a direct effect on cell cycle.

Example 14

Induction of Endothelial Cell Apoptosis by C-CAM1 Mutants Correlated with their Effect on Tumor Suppression The effects of various C-CAM1 mutants on endothelial cell growth were examined in a co-culture system, where HUVECs and DU145 cells were grown respectively in the lower and upper compartments of a multi-well plate, separated by a permeable membrane. Several C-CAM1 mutants were used to infect DU145 cells in the upper compartment: Ad-C-CAM1, Ad-CAM1-cyto (Estrera et al., 1999), Ad-CAM1-gly-cyto (Estrera et al., 1999), and Ad-hu-C-CAM1 (human homologue of C-CAM1) (Luo et al., 1999), which possess tumor suppressor activity. DU145 cells were also infected with control virus or Ad-CAM1-cyto-S503A, which are devoid of suppressor function. After 48 hr of incubation, both DU145 and HUVEC were collected and subjected to PI staining followed by FACS analysis. Significant sub-G1 populations, indicative of apoptosis, were detected in HUVECs only after incubation with C-CAM1 mutants that retained tumor suppressor function. Neither control virus nor Ad-CAM1-cyto-S503A mutant, that lacks tumor suppressor activity, was able to induce apoptosis in HUVECs. Thus, the ability of various C-CAM1 mutants to induce endothelial cell apoptosis closely paralleled their tumor suppressor activity. These observations suggest that C-CAM1-mediated tumor suppression in vivo is, at least in part, due to its ability to inhibit neovascularization by inducing release of anti-angiogenic factor or factors.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,201,767
U.S. Pat. No. 4,587,055
U.S. Pat. No. 5,359,046
U.S. Pat. No. 5,399,363
U.S. Pat. No. 5,466,468
U.S. Pat. No. 5,543,158
U.S. Pat. No. 5,639,725
U.S. Pat. No. 5,641,515
U.S. Pat. No. 5,656,016
U.S. Pat. No. 5,697,899
U.S. Pat. No. 5,733,876
U.S. Pat. No. 5,756,353
U.S. Pat. No. 5,759,566
U.S. Pat. No. 5,762,904
U.S. Pat. No. 5,770,219
U.S. Pat. No. 5,779,708
U.S. Pat. No. 5,783,208
U.S. Pat. No. 5,797,898
U.S. Pat. No. 5,811,128
U.S. Pat. No. 5,846,225
U.S. Pat. No. 5,846,233
EPO 0273085
Arcone et al., *Nucleic Acids Research*, 16(8):3195–3207, 1988.
Altruda et al., *Gene*, 85(2):445–51, 1989.
Aurivillius et al., "The cell adhesion molecule cell-CAM 105 is an ecto-ATPase and a member of the immunoglobulin superfamily," *FEBS Lett.*, 264:267–269, 1990.
Baichwal and Sugden, "Vectors for gene transfer derived from animal DNA viruses: Transient and stable expression of transferred genes," In: Kucherlapati R, ed. Gene transfer. New York: Plenum Press, pp. 117–148, 1986.
Bartlett et al., *Proc. Natl. Acad. Sci. USA*, 93:8852–8857, 1996.
Bedzyk et al., *J. Biol. Chem.*, 265:18615, 1990
Benchimol et al., "Carcinoembryonic antigen, a human tumor marker, functions as an intercellular adhesion molecule," *Cell*, 57:327–334, 1989.
Benvenisty and Neshif, "Direction introduction of genes into rats and expression of the genes," *Proc. Natl. Acad. Sci. USA*, 83:9551–9555, 1986.
Bieber et al., *Cell*, 59(3):447–60, 1989.
Bourlais et al., *Prog. Retin Eye Res.*, 17(1):33–58, 1998.
Cambier and Campbell, "Membrane immunoglobulin and its accomplices: new lessons from an old receptor," *FASEB J.*, 6:3207–3217, 1992.
Capaldi et al., *Biochem. Biophys. Res. Comm.*, 76:425 1977.
Carter and Flotte, *Ann. N.Y. Acad. Sci.*, 770:79–90, 1995.
Chatterjee, et al., *Ann. N.Y. Acad. Sci.*, 770:79–90, 1995.
Chaudhary et al. *Proc. Natl. Acad. Sci.*, 87:9491, 1990
Chen and Okayama, "High-efficiency transfection of mammalian cells by plasmid DNA," *Mol. Cell Biol.*, 7:2745–2752, 1987.
Cheung et al., "Cell-CAM105 isoforms with different adhesion functions are coexpressed in adult rat tissues and during liver development," *J. Biol. Chem.*, 268:6139–6146, 1993b.
Cheung et al., "Structure and function of C-CAM1, "*J. Biol. Chem.*, 268:24303–24310, 1993a.
Cheung et al., "The cytoplasmic domain of C-CAM is required for C-CAM mediated adhesion function: Studies of a C-CAM transcript containing an unspliced intron," *Biochem. J.*, 295:427–435, 1993c.
Coffin, In: *Virology*, ed., New York: Raven Press, pp. 1437–1500, 1990.
Coupar et al., "A general method for the construction of recombinant vaccinia virus expressing multiple foreign genes," *Gene*, 68:1–10, 1988.
Culic et al., "Molecular cloning and expression of a new rat liver cell-CAM 105 isoform," *Biochem. J.*, 285:47–53, 1992.
Dani, et al., *J. Biol. Chem.*, 264:10119–10125, 1989.

Dubensky et al., "Direct transfection of viral and plasmid DNA into the liver or spleen of mice," *Proc. Natl. Acad. Sci. USA,* 81:7529–7533, 1984.

Edelman and Crossin, "Cell Adhesion Molecules: Implications for a Molecular Histology," *Annu. Rev. Biochem.,* 60:155–190, 1991.

Elices et al., *Cell,* 60(4):577–84, 1990.

Fearon et al., *Science,* 247:49, 1990.

Fechheimer et al., "Transfection of mammalian cells with plasmid DNA by scrape loading and sonication loading," *Proc. Natl. Acad. Sci. USA,* 84:8463–8467, 1987.

Ferkol et al., *FASEB J.,* 7:1081–1091, 1993.

Ferrari et al., *J. Virol.,* 70:3227–3234, 1996.

Fidler and Balch, *Curr. Probl. Surg.* 24:137–208, 1987.

Fidler and Ellis, *Cell,* 79:185–188, 1994.

Fidler and Poste, *Semin. Oncol.* 12:207–221, 1985.

Fidler, *J. Natl. Cancer Inst.,* 87:1588, 1995.

Fisher et al., *J. Virol.,* 70:520–532, 1996.

Flotte et al., *Proc. Natl. Acad. Sci. USA,* 90:10613–10617, 1993.

Folkman and Shing, "Angiogenesis," *J. Biol. Chem.,* 267:10931–10934, 1992.

Folkman and Shing, *J. Biol. Chem.,* 267:10931–10934, 1992.

Folkman, "Angiogenesis in cancer, vascular, rheumatoid and other disease," *Nature Medicine,* 1:27–31, 1995.

Folkman, *Cancer Res.* 46, 467–473, 1986.

Folkman, *N Engl J Med.* 285(21): 1182–1186, 1971

Folkman, *N Engl J Med.* 320(18): 1211–1212, 1989

Fraley et al., "Entrapment of a bacterial plasmid in phospholipid vesicles: Potential for gene transfer," *Proc. Natl. Acad. Sci. USA,* 76:3348–3352, 1979.

Furley et al., *Cell,* 61(1):157–70, 1990.

Gall and Edelman, *Science,* 213:903–905, 1981.

Geiger, "Membrane-cytoskeleton interaction," *Biochim. Biophys. Acta,* 737:305–341, 1983.

Gennarini et al., *J. Cell Biol.,* 109(2):775–88, 1989.

Ghosh and Bachhawat, "Targeting of liposomes to hepatocytes," In: Wu G, Wu C ed. Liver diseases, targeted diagnosis and therapy using specific receptors and ligands. New York: Marcel Dekker, pp. 87–104, 1991.

Goodman et al., *Blood,* 84:1492–1500, 1994.

Gopal, "Gene transfer method for transient gene expression, stable transfection, and cotransfection of suspension cell cultures," *Mol. Cell Biol.,* 5:1188–1190, 1985.

Gossen and Bujard, *Proc. Natl. Acad. Sci. USA,* 89:5547–5551, 1992.

Gossen et al., *Science,* 268:1766–1769, 1995.

Graham and Prevec, "Manipulation of adenovirus vector," In: E. J. Murray (ed.), Methods in Molecular Biology: Gene Transfer and Expression Protocol, Clifton, N.J.: Humana Press, 7:109–128, 1991.

Graham and van der Eb, "A new technique for the assay of infectivity of human adenovirus 5 DNA", *Virology,* 52:456–467, 1973.

Grunicke and Maly, "Role of GTPase and GTPase regulatory proteins in oncogenesis," *Crit. Rev. Oncog.,* 4:389–402, 1993.

Hanahan and Folkman, "Patterns and emerging mechanisms of the angiogenic switch during tumorigenesis," *J. Natl. Cancer Inst.,* 88:1091–1092, 1996.

Hansson et al., *Thromb. Res.,* 58(1):61–73, 1990.

Harland and Weintraub, "Translation of mammalian mRNA injected into Xenopus oocytes is specifically inhibited by antisense RNA," *J. Cell Biol.,* 101:1094–1099, 1985.

Harrelson et al., *Science,* 242(4879):700–8, 1988.

Hay et al., *J. Mol. Biol.,* 175:493–510, 1984.

Hearing and Shenk, *J. Mol. Biol.* 167:809–822, 1983.

Hearing et al., *J. Virol.,* 67:2555–2558, 1987.

Hermanson et al., *Proc. Nat'l. Acad. Sci. USA,* 85(18):6890–4, 1988.

Hinson et al., "Alterations in the expression of a hepatocyte cell adhesion molecule by transplantable rat hepatocellular carcinomas," *Cancer Res.,* 45:4742–3749, 1985.

Hixson and McEntire, "Detection of an altered form of cell-CAM105 on rat transplantable and primary hepatocellular carcinomas," *Cancer Res.,* 49:6788–6794, 1989.

Hixson, McEntire, Obrink, *Cancer Res.,* 45:3742–3749, 1985.

Hollstein et al., *Science,* 253:49–53, 1991.

Hsieh et al., "Tumor suppressive role of an androgen-regulated epithelial cell adhesion molecule (C-CAM) in prostate carcinoma cell revealed by sense and antisense approaches," *Cancer Res.,* 55:190–197, 1995.

Hunt et al., *Proc. Natl. Acad. Sci. USA,* 83:3786–3790, 1986.

Hynes, "Integrins: a family of cell surface reeptors," *Cell,* 48:549–554, 1987.

Joki, et al., *Human Gene Ther.,* 6:1507–1513, 1995.

Jones and Shenk, "Isolation of deletion and substitution mutants of adenovirus type 5," *Cell,* 13:181–188, 1978.

Kageyama, et al., *J. Biol. Chem.,* 262(5):2345–2351, 1987.

Kaneda et al., "Increased expression of DNA cointroduced with nuclear protein in adult rat liver," *Science,* 243:375–378, 1989.

Kaplitt et al., *Arm. Thor. Surg.,* 62:1669–1676, 1996.

Kaplitt et al., *Nat. Genet.,* 8:148–153, 1994.

Kato et al., "Expression of hepatitis B virus surface antigen in adult rat liver," *J. Biol. Chem.,* 266:3361–3364, 1991.

Kessler et al., *Proc. Natl. Acad. Sci. USA,* 93:14082–14087, 1996.

Khan et al., "Molecular cloning and expression of cDNA for carcinoembryonic antigen-related glycoproteins: the pregnancy-specific β-glycoprotein fetal liver NCA superfamily," *In The Carcinoembryonic Antigen Gene Family* (eds. A. Yachi and J E. Shively)., pp. 87–96, Elsevier Science Publishers, 1989.

Klein et al., "High-velocity microprojectiles for delivering nucleic acids into living cells," *Nature,* 327:70–73, 1987.

Kleinernan et al., "Application of a tumor suppressor (C-CAM1)-expressing recombinant adenovirus in androgen-independent human prostate cancer therapy: A preclinical study," *Cancer Res.,* 55:2831–2836, 1995.

Kleinerman, Troncoso, Lin, Pisters, Sherwood, Brooks, von Eschenbach, Hsieh, *Cancer Res.,* 55:1215–1220, 1995a.

Kleinerman, Zhang, Lin, Nguyen, von Eschenbach, Hsieh, *Cancer Res.,* 55:2831–2836, 1995b.

Koeberl et al., *Proc. Natl. Acad. Sci. USA,* 94:1426–1431, 1997.

Korhonen, et al., Blood, Vol. 86, No. 5, Sep. 1, 1995: pp 1828–1835.

Laemmli, "Cleavage of structural proteins during the assembly of the head of bacteriophage T4," *Nature,* 227:680–685, 1970.

Lehmann et al., *Proc. Natl. Acad. Sci. USA,* 86(24):9891–5, 1989.

Lemke et al., *Neuron.,* 1(1):73–83, 1988.

Levrero et al., "Defective and nondefective adenovirus vectors for expressing foreign genes in vitro and in vivo," *Gene,* 101: 195–202, 1991.

Lin and Guidotti, *J. Biol. Chem.,* 264:14408–14414, 1989.

Lin et al., "Immunochemical characterization of two isoforms of rat liver ecto-ATPase that show an immunological and structural identity with a glycoprotein cell-adhesion molecule with $M_r$ 105000," *Biochem. J.,* 278:155–161, 1991.

Lin, Culic, Flangan, Hixson, *Biochem. J.,* 278:155–161, 1991.

Linsley et al., *Proc. Natl. Acad. Sci. USA,* 87(13):5031–5, 1990.

Lou, Talposky, Earley, Wood, Wilson, Logothetis, *Cancer Gene Ther.,* in press.

Lou, Wood, Earley, Hung, Lin, *Oncogene,* 14:1697–1704, 1997.

Luna and Hitt, "Cytoskeleton-plasma membrane interactions," *Science,* 258:955–964, 1992.

Macejak and Sarnow, *Nature,* 353:90–94, 1991.

Mann et al., "Construction of a retrovirus packaging mutant and its use to produce helper-free defective retrovirus," *Cell,* 33:153–159, 1983.

Marx, "Learning how to suppress cancer," *Science,* 261:1385–1387, 1993.

McCown et al., *Brain Res.,* 713:99–107, 1996.

Mizukami et al., *Virology,* 217:124–130, 1996.

Moos et al., *Nature,* 334(6184):701–3, 1988.

Neumaier et al., "Biliary glycoprotein, a potential human cell adhesion molecule, is down-regulated in colorectal carcinomas," *Proc. Natl. Acad. Sci. USA,* 90:10744–10748, 1993.

Newman et al., *Science,* 247(4947):1219–22, 1990.

Nicolas and Rubenstein, "Retroviral vectors," In: Rodriguez R L, Denhardt D T, ed. Vectors: A survey of molecular cloning vectors and their uses. Stoneham: Butterworth, pp. 493–513, 1988.

Nicolau and Sene, "Liposome-mediated DNA transfer in eukaryotic cells," *Biochim. Biophys. Acta,* 721:185–190, 1982.

Nicolau et al., "Liposomes as carriers for in vivo gene transfer and expression," *Methods Enzymol.,* 149:157–176, 1987.

Obrink, "C-CAM (Cell-CAM 105)- a member of the growing immunoglobulin superfamily of cell adhesion proteins," *BioEssays.,* 13:227–233, 1991.

Ocklind and Obrink, *J. Biol. Chem.,* 257:6788–6795, 1982.

Odin et al., "Chemical characterization of cell-CAM 105, a cell adhesion molecule isolated from rat liver membranes," *Biochem. J.,* 236:559–568, 1986.

Odin et al., "Immunohistochemical localization of cell-CAM 105 in rat tissues. Appearance in epithelia, platelets and granulocytes.," *J. Histochem. Cytochem.,* 36:729–739, 1988.

Oikawa et al., "Cell adhesion activity of non-specific cross-reacting antigen (NCA) and carcinoembryonic antigen (CEA) expressed on CHO cell surface: homophilic and heterophilic adhesion," *Biochem. Biophys. Rev. Commun.,* 164:39–45, 1989.

Olivierio, et al., *EMBO J.,* 6(7):1905–1912, 1987.

Pape and Kim, *Mol. Cell. Biol.,* 974–982, 1989.

Paskind et al., "Dependence of moloney murine leukemia virus production on cell growth," *Virology,* 67:242–248, 1975.

Pelletier and Sonenberg, *Nature,* 334:320–325, 1988.

Perales et al., *Proc. Natl. Acad. Sci.* 91:4086–4090, 1994.

Ping et al., *Microcirculation,* 3:225–228, 1996.

Poli and Cortese, *Proc. Natl. Acad. Sci. USA,* 86:8202–8206, 1989.

Pollerberg et al., *Nature,* 324:462–465, 1986.

Potter et al., "Enhancer-dependent expression of human k immunoglobulin genes introduced into mouse pre-B lymphocytes by electroporation," *Proc. Nat'l Acad. Sci. USA,* 81:7161–7165, 1984.

Prowse and Baumann, *Mol Cell Biol,* 8(1):42–51, 1988.

Radler et al., *Science,* 275:810–814, 1997.

Rak, St Croix, Kerbel, *Anticancer Drugs,* 6:3–18, 1995.

Ranscht, *J. Cell Biol.,* 107(4):1561–73, 1988.

Renan, "Cancer genes: current status, future prospects, and applicants in radiotherapy/oncology," *Radiother. Oncol.,* 19:197–218, 1990.

Ridgeway, "Mammalian expression vectors," In: Rodriguez R L, Denhardt D T, ed. Vectors: A survey of molecular cloning vectors and their uses. Stoneham: Butterworth, pp. 467–492, 1988.

Rippe et al., "DNA-mediated gene transfer into adult rat hepatocytes in primary culture," *Mol. Cell Biol.,* 10:689–695, 1990.

Rockwell, et al., "Characteristics of a serially transplanted mouse mammary tumor and its tissue-culture-adapted derivative," *J. Natl. Cancer Inst.,* 49:735–749, 1972.

Ron, et al., *Mol. Cell. Biol.,* 2887–2895, 1991.

Rosenberg et al., "The expression of mouse biliary glycoprotein, a carcinoembryonic antigen-related gene, is down-regulated in malignant mouse tissues," *Cancer Res.,* 53:4938–4945, 1993.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA,* 86:9079–9083, 1989.

Rubinfeld et al., "Association of the APC gene product with β-catenin," *Science,* 262:1731–1734, 1993.

Salzer et al., *J. Cell Biol.,* 104(4):957–65, 1987.

Samulski et al., *J. Virol.,* 61(10):3096–3101, 1987.

Seeger et al., *Cell,* 55(4):589–600, 1988.

Serrano et al., *Nature,* 366:704–707, 1993.

Serrano et al., *Science,* 267:249–252, 1995.

Speigelman, et al., *J. Biol. Chem.,* 264(3), 1811–1815, 1989.

Staunton et al., *Cell,* 52(6):925–33, 1988.

Stone, Mickey, Wunderli, Mickey, Paulson, *Int. J. Cancer,* 21:274–281, 1978.

Stoolman, "Adhesion molecules controlling lymphocyte migration," *Cell,* 56:907–910, 1989.

Streuli et al., *J. Exp. Med.,* 168(5):1523–30, 1988.

Su et al., "Association of the APC tumor suppressor protein with catenins," *Science,* 262:1734–1737, 1993.

Sugarbaker, *Curr. Prob. Cancer* 3:1–59, 1979.

Suzuki et al., *FEBS Lett.,* 425(3):436–40, 1998.

Takeichi, "Cadherin cell adhesion receptors as a morphogenetic regulator," *Science,* 251:1451–1455, 1991.

Takeichi, "The cadherins: cell-cell adhesion molecules controlling animal morphogenesis," *Development,* 102:639–655, 1988.

Temin, "Retrovirus vectors for gene transfer: Efficient integration into and expression of exogenous DNA in vertebrate cell genome," In: Kucherlapati R, ed. Gene transfer. New York: Plenum Press, pp.149–188, 1986.

Tibbetts *Cell,* 12:243–249, 1977.

Tingstrom et al., *J. Cell Sci.,* 96:17–25, 1990.

Trofatter et al., "A novel moesin-, ezrin-, radixin-like gene is a candidate for the neurofibromatosis 2 tumor suppressor," *Cell,* 72:791–800, 1993.

Tur-Kaspa et al., "Use of electroporation to introduce biologically active foreign genes into primary rat hepatocytes," *Mol. Cell Biol.,* 6:716–718, 1986.

Wagner et al., *Proc. Natl. Acad. Sci.* 87(9):3410–3414, 1990.

Wagner et al., *Science,* 260:1510–1513, 1993.

Walther and Stein, *J. Mol. Med,* Vol. 74, 1996: pp. 379–392.

Watt et al., *Proc. Natl Acad. Sci.,* 83(2): 3166–3170, 1986.

Weidner, Carroll, Flax et al., "Tumor angiogenesis correlates with metastasis in invasive prostate carcinoma, *Am. J. Pathol.,* 143:401–409, 1993.

Weidner, Semple, Welch, "Tumor angiogenesis and metastasis-correlation in invasive breast carcinoma," *N. Engl. J Med.,* 324:1–8, 1991.

Weinberg, *Science,* 254:1138–1145, 1991.

Williams and Barclay, *Annu. Rev. Immunol.,* 6:381–405, 1988.

Wilson, et al., *Mol. Cell. Biol.,* 6181–6191, 1990.

Wong et al., "Appearance of β-lactamase activity in animal cells upon liposome mediated gene transfer," *Gene,* 10:87–94, 1980.

Wu and Wu, "Evidence for targeted gene delivery to HepG2 hepatoma cells in vitro," *Biochemistry,* 27:887–892, 1988.

Wu and Wu, "Receptor-mediated in vitro gene transfections by a soluble DNA carrier system," *J. Biol. Chem.,* 262:4429–4432, 1987.

Wu and Wu, *Adv. Drug Delivery Rev.,* 12:159–167, 1993.

Xiao et al., *J. Virol.,* 70:8098–8108, 1996.

Yang et al., "In vivo and in vitro gene transfer to mammalian somatic cells by particle bombardment," *Proc. Natl. Acad. Sci. USA,* 87:9568–9572, 1990.

Zechner, et al., *Mol. Cell. Biol.,* 2394–2401, 1988.

Zhang et al., "Generation and identification of recombinant adenovirus by liposome-mediated transfection and PCR™ analysis," *Biotechniques,* 15:868–872, 1993.

What is claimed is:

1. A composition comprising an expression construct comprising a nucleic acid sequence encoding SEQ ID NO:1, wherein the nucleic acid sequence does not encode other C-CAM1 domains, and wherein the nucleic acid sequence is under the transcriptional control of a promoter operable in a eukaryotic cell.

2. The composition of claim 1, wherein the expression construct is an adenovirus, an adeno-associated virus, a vaccinia virus, or a herpes virus.

3. The composition of claim 2, wherein the expression construct is an adenovirus.

4. The composition of claim 1, wherein the expression construct is a non-viral vector.

5. The composition of claim 1, wherein the promoter is CMV IE, human or murine MHC class II, SV40, RSV LTR, HIV-1 LTR, or HIV-2 LTR.

6. The composition of claim 1, wherein the composition is in a pharmaceutically acceptable formulation.

7. A composition comprising an adenovirus expression construct comprising a nucleic acid sequence encoding SEQ ID NO:1, wherein the nucleic acid sequence does not encode other C-CAM1 domains, and wherein the nucleic acid sequence is under the transcriptional control of a promoter operable in a eukaryotic cell.

8. The composition of claim 7, wherein the promoter is CMV IE.

9. A composition in a pharmaceutically acceptable formulation comprising an adenovirus expression construct comprising a nucleic acid sequence encoding SEQ ID NO:1, wherein the nucleic acid sequence does not encode other C-CAM1 domains, and wherein the nucleic acid sequence is under the transcriptional control of a promoter operable in a eukaryotic cell.

\* \* \* \* \*

UNITED STATES PATENT AND TRADEMARK OFFICE
CERTIFICATE OF CORRECTION

| | |
|---|---|
| PATENT NO. | : 6,517,828 B1 |
| APPLICATION NO. | : 09/580043 |
| DATED | : February 11, 2003 |
| INVENTOR(S) | : Sue-Hwa Lin, Weiping Luo and Christopher Logothetis |

It is certified that error appears in the above-identified patent and that said Letters Patent is hereby corrected as shown below:

Col. 1, In. 6, delete "The U.S. government may own rights in this invention pursuant to grant number 5RO1CA64856 from the National Cancer Institute." and insert therefor --This invention was made with government support under 5RO1CA64856 awarded by the National Cancer Institute. The government has certain rights in the invention.--

Signed and Sealed this

Fifteenth Day of January, 2008

JON W. DUDAS
*Director of the United States Patent and Trademark Office*

SEQUENCE LISTING

```
<160> NUMBER OF SEQ ID NOS: 9

<210> SEQ ID NO 1
<211> LENGTH: 74
<212> TYPE: PRT
<213> ORGANISM: Homo sapiens

<400> SEQUENCE: 1

His Phe Gly Lys Thr Gly Arg Ala Ser Asp Gln Arg Asp Leu Thr Glu
 1               5                  10                  15

His Lys Pro Ser Val Ser Asn His Thr Gln Asp His Ser Asn Asp Pro
                20                  25                  30

Pro Asn Lys Met Asn Glu Val Thr Tyr Ser Thr Leu Asn Phe Glu Ala
            35                  40                  45

Gln Gln Pro Thr Gln Pro Thr Ser Ala Ser Pro Ser Leu Thr Ala Thr
        50                  55                  60

Glu Ile Ile Tyr Ser Glu Val Lys Lys Gln
 65                  70

<210> SEQ ID NO 2
<211> LENGTH: 73
<212> TYPE: PRT
<213> ORGANISM: Mus musculus

<400> SEQUENCE: 2

Ser Arg Lys Ser Gly Gly Gly Ser Asp Gln Arg Asp Leu Thr Glu His
 1               5                  10                  15

Lys Pro Ser Thr Ser Asn His Asn Leu Ala Pro Ser Asp Asn Ser Pro
                20                  25                  30

Asn Lys Val Asp Asp Val Ala Tyr Thr Val Leu Asn Phe Asn Ser Gln
            35                  40                  45

Gln Pro Asn Arg Pro Thr Ser Ala Pro Ser Ser Pro Arg Ala Thr Glu
        50                  55                  60

Thr Val Tyr Ser Glu Val Lys Lys Lys
 65                  70

<210> SEQ ID NO 3
<211> LENGTH: 71
<212> TYPE: PRT
<213> ORGANISM: Rattus norvegicus

<400> SEQUENCE: 3

Ser Arg Lys Thr Gly Gly Gly Ser Asp His Arg Asp Leu Thr Glu His
 1               5                  10                  15

Lys Pro Ser Thr Ser Ser His Asn Leu Gly Pro Ser Asp Asp Ser Pro
```

```
                    20                  25                  30
Asn Lys Val Asp Asp Val Ser Tyr Ser Val Leu Asn Phe Asn Ala Gln
                35                  40                  45

Gln Ser Lys Arg Pro Thr Ser Ala Ser Ser Ser Pro Thr Glu Thr Val
    50                  55                  60

Tyr Ser Val Val Lys Lys Lys
 65                  70
```

```
<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 4
aagcttatgg gatccaggaa gactggcggg gga                              33

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 5
aagcttatgg gatccaggaa gactggcggg gga                              33

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 6
ggcccacccc cttggcttc                                              19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 7
ttgtaaccat tataagctgc                                             20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 8
tcgtttctca gcagctgttg                                             20

<210> SEQ ID NO 9
<211> LENGTH: 20
```

-continued

```
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 9
catctgaact caaagcgtgg                                                      20
```